(12) United States Patent
Gillberg et al.

(10) Patent No.: US 9,993,172 B2
(45) Date of Patent: Jun. 12, 2018

(54) NONINVASIVE CARDIAC THERAPY EVALUATION

(71) Applicant: Medtronic, Inc., Minneapolis, MN (US)

(72) Inventors: Jeffrey Gillberg, Coon Rapids, MN (US); Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 186 days.

(21) Appl. No.: 14/228,024

(22) Filed: Mar. 27, 2014

(65) Prior Publication Data

US 2015/0157232 A1 Jun. 11, 2015

Related U.S. Application Data

(60) Provisional application No. 61/913,743, filed on Dec. 9, 2013.

(51) Int. Cl.
*A61B 5/044* (2006.01)
*A61B 5/0408* (2006.01)
(Continued)

(52) U.S. Cl.
CPC .......... *A61B 5/0408* (2013.01); *A61B 5/0402* (2013.01); *A61B 5/044* (2013.01); *A61B 5/0452* (2013.01); *A61B 5/04085* (2013.01); *A61B 5/743* (2013.01); *A61N 1/368* (2013.01); *A61N 1/3702* (2013.01); *G06F 19/3481* (2013.01); *G16H 40/63* (2018.01); *G16H 50/30* (2018.01); *G16H 50/70* (2018.01); *A61B 5/0472* (2013.01); *A61B 5/1107* (2013.01); *A61B 5/6823* (2013.01); *A61N 1/3627* (2013.01); *A61N 1/36507* (2013.01)

(58) Field of Classification Search
CPC ........................... A61N 1/3627; A61N 1/3684
See application file for complete search history.

(56) References Cited

U.S. PATENT DOCUMENTS

| | | | |
|---|---|---|---|
| 4,233,987 | A | 11/1980 | Feingold |
| 4,402,323 | A | 9/1983 | White |

(Continued)

FOREIGN PATENT DOCUMENTS

| | | | |
|---|---|---|---|
| CN | 1043621 | A | 11/1990 |
| CN | 1253761 | A | 5/2000 |

(Continued)

OTHER PUBLICATIONS

International Search Report / Written Opinion, dated Aug. 6, 2014; Patent Application No. PCT/US2014/036153, filed Apr. 30, 2014; 14 pages.

(Continued)

*Primary Examiner* — Michael D Abreu

(57) ABSTRACT

Systems, methods, and interfaces are described herein for assisting a user in noninvasive evaluation of patients for cardiac therapy and noninvasive evaluation of cardiac therapy being delivered. The systems, methods, and interfaces may provide graphical representations of cardiac electrical activation times about one or more portions of human anatomy and one or more cardiac health metrics.

21 Claims, 14 Drawing Sheets

(51) Int. Cl.
  *A61B 5/0452*   (2006.01)
  *A61N 1/368*    (2006.01)
  *A61N 1/37*     (2006.01)
  *A61B 5/00*     (2006.01)
  *A61B 5/0402*   (2006.01)
  *G06F 19/00*    (2018.01)
  *A61B 5/0472*   (2006.01)
  *A61B 5/11*     (2006.01)
  *A61N 1/365*    (2006.01)
  *A61N 1/362*    (2006.01)

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A * | 5/1996 | Markowitz ........... A61N 1/3627 607/9 |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A * | 4/1999 | Albrecht ............ A61B 5/04085 600/509 |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harley et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,527,051 B1 | 9/2013 | Hedberg et al. |
| 8,583,230 B2 | 11/2013 | Ryu et al. |

(56) References Cited

U.S. PATENT DOCUMENTS

| | | |
|---|---|---|
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1* | 3/2008 | Costello ............... A61B 5/1107 600/508 |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1* | 9/2010 | Olson ................ A61B 5/04011 600/509 |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1* | 11/2012 | Gosh ................ A61B 5/0402 703/2 |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |

(56) References Cited

U.S. PATENT DOCUMENTS

| | | |
|---|---|---|
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Ghosh et al. |
| 2016/0184590 A1 | 6/2016 | Gosh |

FOREIGN PATENT DOCUMENTS

| | | |
|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 98/26712 A1 | 6/1998 |
| WO | WO 1999/006112 A1 | 2/1999 |
| WO | WO 00/45700 | 8/2000 |
| WO | WO 01/67950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | PCT/US2014/036153 | 4/2014 |
| WO | PCT/US2014/036163 | 4/2014 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report / Written Opinion, dated Nov. 7, 2014; Patent Application No. PCT/US2014/036163, filed Apr. 30, 2014; 12 pages.
International Search Report / Written Opinion, dated Oct. 28, 2014; Patent Application No. PCT/US2014/041928, filed Jun. 11, 2014; 15 pages.
International Search Report / Written Opinion, dated Oct. 24. 2014; Patent Application No. PCT/US2014/041929, filed Jun. 11, 2014; 15 pages.
U.S. Appl. No. 13/916,353, filed Jun. 12, 2013, Ghosh.
U.S. Appl. No. 13/916,377, filed Jun. 12, 2013, Ghosh.
U.S. Appl. No. 13/952,043, filed Jul. 26, 2013, Ghosh.
U.S. Appl. No. 13/952,061, filed Jul. 26, 2013, Ghosh.
U.S. Appl. No. 14/190,508, filed Feb. 26, 2014.
U.S. Appl. No. 14/190,578, filed Feb. 26, 2014.
U.S. Appl. No. 14/220,733, filed Mar. 20, 2014, Ghosh et al.
U.S. Appl. No. 14/227,719, filed Mar. 27, 2014, Gillberg et al.
U.S. Appl. No. 14/227,919, filed Mar. 27, 2014, Ghosh et al.
U.S. Appl. No. 14/227,955, filed Mar. 27, 2014, Ghosh et al.
U.S. Appl. No. 14/227,962, filed Mar. 27, 2014, Ghosh et al.
U.S. Appl. No. 14/228,009, filed Mar. 27, 2014, Gillberg et al.
U.S. Appl. No. 14/228,024, filed Mar. 27, 2014, Ghosh et al.
U.S. Appl. No. 14/228,038, filed Mar. 27, 2014, Ghosh et al.
International Search Report and Written Opinion for PCT/US2014/036262, dated May 3, 2012; 9 pg.
International Search Report and Written Opinion for PCT/US2014/036302, dated May 3, 2012; 9 pg.
"CardioGuide System Enables Real-Time Navigation of Left Ventricular Leads During Medtronic CRT Implants," Press Release, Apr. 9, 2013, Medtronic, Inc., 2 pgs.
Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.

(56) References Cited

OTHER PUBLICATIONS

Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages, Retrieved from the Internet: Jun. 19, 2014 http://www.mathworks.com/matlabcentral/fileexchange/52-regtools.
"Heart Failure Management" datasheet [online]. Medtronic, Minneapolis, Minnesota, [Last updated on Jun. 3, 2013].Retrieved from the Internet: www.medtronic.com; 9 pages.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms : a simulation study," Circulation Research, 1989, 64:449-462.
Sweeney et al., "Analysis of Ventricular Activation Using Surface Electrocardiography to Predict Left Ventricular Reverse Volumetric Remoldeling During Cardiac Resynchronization Therapy," *Circulation*, Feb. 9, 2010; 121(5):626-34. Available online Jan. 25, 2010.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Varma et al., "Placebo CRT," *Journal of Cardiovascular Electrophysiology*, vol. 19, Aug. 2008; p. 878.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
International Search Report and Written Opinion dated Mar. 9, 2015, for International Application No. PCT/US2014/069214.
International Search Report and Written Opinion dated Mar. 17, 2015, for International Application No. PCT/US2014/069192.
International Search Report and Written Opinion dated Mar. 16, 2015, for International Application No. PCT/US2014/069182.
U.S. Appl. No. 14/173,288, filed Feb. 5, 2014, Sambelashvili.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Hayes et al., "Cardiac Resynchronization Therapy and the Relationship of Percent Biventricular Pacing to Symptoms and Survival," *Heart Rhythm*, Sep. 2011; 8(9):1469-1475.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
International Search Report and Written Opinion dated May 3, 2012 for International Application No. PCT/US2012/036262; 9 pages.
International Search Report and Written Opinion dated May 3, 2012 for International Application No. PCT/US2012/036302; 9 pages.
International Search Report and Written Opinion dated on Apr. 8, 2015, for International Application No. PCT/US2014/069070; 11 pages.
International Search Report and Written Opinion for PCT/US2014/0247583, dated Nov. 4, 2014; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
Cuculich et al., "The Electrophysiological Cardiac Ventricular Substrate in Patients After Myocardial Infarction," *J. Am. Coll. Cardiol.*, 2011; 58:1893-1902.
Dawoud et al., "Inverse Electrocardiographic Imaging to Assess Electrical Dyssynchrony in Cardiac Resynchronization Therapy Patients," *Computing in Cardiology*, 2012; 39:993-996.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Medtronic Vitatron Carelink Encore® Programmer Model 29901 Reference Manual, 2013, Medtronic, Inc., Minneapolis, MN.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Strik et al., "Electrical and Mechanical Ventricular Activation During Left Bundle Branch Block and Resynchronization," *J. of Cardiovasc. Trans. Res.*, 2012; 5:11-126.
International Search Report and Written Opinion dated Jun. 11, 2015 for International Application No. PCT/US2015/021442; 13 pages.
Miri et al., "Applicability of body surface potential map in computerized optimization of biventricular pacing," *Annals of Biomedical Engineering*, vol. 38, No. 3, Mar. 2010, pp. 865-875.
Miri et al., "Comparison of the electrophysiologically based optimization methods with different pacing parameters in patient undergoing resynchronization treatment," $30^{th}$ *Annual International IEEE EMBS Conference*, Aug. 2008, pp. 1741-1744.
Miri et al., "Computerized Optimization of Biventricular Pacing Using Body Surface Potential Map," $31^{st}$ *Annual International Conference of the IEEE EMBS*, Sep. 2009, pp. 2815-2818.
Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.
Svendsen et al., "Computational Models of Cardiac Electrical Activation," Chapter 5, Computational Nov. 2010, pp. 73-88.
Wang et al., "Application of the Method of Fundamental Solutions to Potential-based Inverse Electrocardiography," *Annals of Biomedical Engineering*, Aug. 2006, pp. 1272-1288.
Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.

(56) References Cited

OTHER PUBLICATIONS

Fung et al., Chapter 20, Optimization of Cardiac Resynchronization Therapy, Cardiac Resynchronization Therapy, Second Edition, Copyright 2008, Blackwell Publishing Ltd., pp. 356-373.

Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.

Nash et al., "An Experimental-Computational Framework for Validating in-vivo ECG Inverse Algorithms," International Journal of Bioelectromagnetism, vol. 2, No. 2, Dec. 31, 2000, 9 pp.

Sweeney et al., QRS Fusion Complex Analysis Using Wave Interference to Predict Reverse Remodeling During Cardiac Resynchronization Therapy, heart Rhythm, 2014, 11:806-813.

Wellens, MD et al., "The Electrocardiogram 102 Years After Einthoven," Circulation, Feb. 2004; vol. 109, No. 5, pp. 562-564.

\* cited by examiner

NONINVASIVE CARDIAC THERAPY EVALUATION

CROSS-REFERENCE TO RELATED APPLICATION

This application claims the benefit of U.S. Provisional Patent Application 61/913,743 entitled "Noninvasive Cardiac Therapy Evaluation" and filed on Dec. 9, 2013, which is incorporated herein by reference in its entirety.

BACKGROUND

The disclosure herein relates to systems, methods, and interfaces for use in the noninvasive evaluation of patients for cardiac therapy and noninvasive evaluation of cardiac therapy being performed on patients.

Cardiac therapy, such as cardiac resynchronization therapy (CRT), may correct symptoms of electrical dyssynchrony of a patient's heart by providing pacing therapy to one or both ventricles or atria, e.g., by providing pacing to encourage earlier activation of the left or right ventricles. By pacing the contraction of the ventricles, the ventricles may be controlled so that the ventricles contract in synchrony. Some patients undergoing cardiac therapy have experienced improved ejection fraction, increased exercise capacity, and an improved feeling of well-being.

Providing cardiac therapy to a patient may involve determining whether the patient will derive benefit from the cardiac therapy prior to implantation of a cardiac rhythm device, determining optimal site for placement of one or more ventricular pacing leads, and programming of device parameters, such as selection of electrodes on multi polar right or left ventricular leads, as well as selection of the timing of the pacing pulses delivered to the electrodes, such as atrioventricular (A-V) and intra-ventricular (V-V) delays.

SUMMARY

The exemplary systems, methods, and interfaces described herein may be configured to assist a user (e.g., a physician) in evaluating a patient for cardiac therapy and/or evaluating on-going cardiac therapy (e.g., cardiac therapy being performed on a patient). The systems, methods, and interfaces may be described as being noninvasive. For example, the systems, methods, and interfaces may not use implantable devices such as leads, probes, catheters, etc. to evaluate a patient for cardiac therapy and/or to evaluate on-going cardiac therapy. Instead, the systems, methods, and interfaces may use electrical measurements taken noninvasively using, e.g., a plurality of external electrodes attached to the skin of a patient about the patient's torso.

More specifically, the exemplary systems and methods may provide graphical user interfaces configured to assist a user in ascertaining, or assessing, whether a patient may benefit from cardiac therapy and/or whether cardiac therapy being delivered to the patient is beneficial. The exemplary graphical user interfaces may be configured to display electrical activation times about one or more portions of human anatomy, one or more metrics of the patient's cardiac health, and an indication of whether cardiac therapy may be beneficial for the patient and/or whether the on-going cardiac therapy appears to be beneficial (e.g., when compared to the patient's cardiac health prior to cardiac therapy, etc.).

An exemplary system for assisting in noninvasive evaluation of a patient for cardiac therapy may include electrode apparatus, a display apparatus, and computing apparatus coupled to the electrode apparatus and the display apparatus. The electrode apparatus may include a plurality of external electrodes configured to be located proximate tissue of a patient (e.g., surface electrodes positioned in an array configured to be located proximate the skin of the torso of the patient). The display apparatus may include a graphical user interface configured to present cardiac electrical activation time information and cardiac health information. The computing apparatus may be configured to provide the graphical user interface displayed on the display apparatus to assist a user in noninvasively evaluating the patient for cardiac therapy. The computing apparatus may be further configured to: measure surrogate cardiac electrical activation times using one or more external electrodes of the plurality of external electrodes of the electrode apparatus proximate the patient's heart, display, on the graphical user interface, a graphical representation of the measured surrogate cardiac electrical activation times about a portion of human anatomy (e.g., color scaling the portion of human anatomy on the graphical user interface according to the measured surrogate cardiac electrical activation times), measure at least one metric of the patient's cardiac health (e.g., QRS width, electrical dyssynchrony, etc.) using one or more external electrodes of the plurality of external electrodes of the electrode apparatus proximate the patient's heart, display, on the graphical user interface, the at least one metric of the patient's cardiac health, and display, on the graphical user interface, an indication of whether cardiac therapy for the patient may be beneficial.

An exemplary computer-implemented method for assisting in noninvasive evaluation of a patient for cardiac therapy may include measuring surrogate cardiac electrical activation times using one or more external electrodes proximate the patient's heart (e.g., surface electrodes positioned in an array configured to be located proximate the skin of the torso of the patient), displaying a graphical user interface a graphical representation of the measured surrogate cardiac electrical activation times about a portion of human anatomy (e.g., color scaling the portion of human anatomy on the graphical user interface according to the measured surrogate cardiac electrical activation times), measuring at least one metric of the patient's cardiac health (e.g., QRS width, electrical dyssynchrony, etc.) using one or more external electrodes proximate the patient's heart, displaying, on the graphical user interface, the at least one metric of the patient's cardiac health, and displaying, on the graphical user interface, an indication of whether cardiac therapy for the patient may be beneficial.

Another exemplary system for assisting in noninvasive evaluation of a patient for cardiac therapy may include means for measuring surrogate cardiac electrical activation times representative of the electrical activation times of a patient's heart, means for measuring at least one metric of the patient's cardiac health (e.g., QRS width, electrical dyssynchrony, etc.), display means for displaying, on a graphical user interface, a graphical representation of the measured surrogate cardiac electrical activation times about a portion of human anatomy (e.g., color scaling the portion of human anatomy on the graphical user interface according to the measured surrogate cardiac electrical activation times), the at least one metric of the patient's cardiac health, and an indication of whether cardiac therapy for the patient may be beneficial.

In one or more exemplary embodiments, displaying the graphical representation of the measured surrogate cardiac electrical activation times about a portion of human anatomy may include displaying a graphical representation of the measured surrogate cardiac electrical activation times about a graphical representation of at least one of an anterior side of a human torso and a posterior side of a human torso.

In one or more exemplary embodiments, displaying the graphical representation of the measured surrogate cardiac electrical activation times about a portion of human anatomy may include displaying a graphical representation of the measured surrogate cardiac electrical activation times about a graphical representation of at least one of an anterior side of a heart and a posterior side of a heart.

One or more exemplary embodiments may further include displaying, on the graphical user interface, at least one electrocardiogram of the patient, wherein each of the at least one electrocardiogram are captured using at least one different electrode, and wherein the at least one electrocardiogram is time-aligned on the graphical user interface and/or storing the surrogate cardiac electrical activation times, the at least one metric of the patient's cardiac health, and the at least one electrocardiogram for use in comparisons at a later time.

An exemplary system for assisting in noninvasive evaluation of cardiac therapy may include electrode apparatus, a display apparatus, and computing apparatus coupled to the electrode apparatus and the display apparatus. The electrode apparatus may include a plurality of external electrodes configured to be located proximate tissue of a patient (e.g., surface electrodes positioned in an array configured to be located proximate the skin of the torso of the patient). The display apparatus may include a graphical user interface configured to present cardiac electrical activation time information and cardiac health information. The computing apparatus may be configured to provide the graphical user interface displayed on the display apparatus to assist a user in noninvasively evaluating cardiac therapy. The computing apparatus may be further configured to measure surrogate cardiac electrical activation times using one or more external electrodes of the plurality of external electrodes of the electrode apparatus proximate the patient's heart, display, on the graphical user interface, a graphical representation of presently-measured surrogate cardiac electrical activation times about a first human anatomy portion and a graphical representation of previously-measured surrogate cardiac electrical activation times about a second human anatomy portion (e.g., the first human anatomy portion and the second human anatomy portion may depict the same human anatomy), measure at least one metric of the patient's cardiac health (e.g., QRS width, electrical dyssynchrony, etc.) using one or more external electrodes of the plurality of external electrodes of the electrode apparatus proximate the patient's heart, display, on the graphical user interface, at least one presently-measured metric of the patient's cardiac health and at least one previously-measured metric of the patient's cardiac health, and display, on the graphical user interface, an indication of whether cardiac therapy for the patient appears to be beneficial (e.g., a percentage improvement between the at least one previously-measured metric of the patient's cardiac health and the at least one presently-measured metric of the patient's cardiac health).

One exemplary method for assisting in noninvasive evaluation of cardiac therapy may include measuring surrogate cardiac electrical activation times using one or more external electrodes proximate the patient's heart and displaying a graphical user interface. The graphical user interface may include a graphical representation of presently-measured surrogate cardiac electrical activation times about a first human anatomy portion, and a graphical representation of previously-measured surrogate cardiac electrical activation times about a second human anatomy portion (e.g., the first human anatomy portion and the second human anatomy portion may depict the same human anatomy). The exemplary method may further include measuring at least one metric of the patient's cardiac health (e.g., QRS width, electrical dyssynchrony, etc.) using one or more external electrodes proximate the patient's heart and displaying, on the graphical user interface, at least one presently-measured metric of the patient's cardiac health and at least one previously-measured metric of the patient's cardiac health, and displaying, on the graphical user interface, an indication of whether cardiac therapy for the patient appears to be beneficial (e.g., a percentage improvement between the at least one previously-measured metric of the patient's cardiac health and the at least one presently-measured metric of the patient's cardiac health).

One exemplary system for assisting in noninvasive evaluation of a patient for cardiac therapy may include means for measuring surrogate cardiac electrical activation times representative of the electrical activation times of a patient's heart, means for measuring at least one metric of the patient's cardiac health (e.g., QRS width, electrical dyssynchrony, etc.), and display means for displaying, on a graphical user interface, a graphical representation of presently-measured surrogate cardiac electrical activation times about a first human anatomy portion and a graphical representation of previously-measured surrogate cardiac electrical activation times about a second human anatomy portion (e.g., the first human anatomy portion and the second human anatomy portion may depict the same human anatomy), at least one presently-measured metric of the patient's cardiac health and at least one previously-measured metric of the patient's cardiac health, and an indication of whether cardiac therapy for the patient appears to be beneficial (e.g., a percentage improvement between the at least one previously-measured metric of the patient's cardiac health and the at least one presently-measured metric of the patient's cardiac health).

One or more exemplary embodiments may further include allowing the user to change at least one pacing parameter of an implantable medical device providing cardiac therapy to the patient (e.g., at least one of a pacing timing interval, a pacing vector, and a pacing mode) and/or displaying, on the graphical user interface, mechanical motion information of one or more regions of at least a portion of blood vessel anatomy of the patient's heart.

In one or more exemplary embodiments, displaying graphical representations of the measured surrogate cardiac electrical activation times about the first and second human anatomy portions may include displaying graphical representations of the measured surrogate cardiac electrical activation times about graphical representations of at least one of an anterior side of a human torso and a posterior side of a human torso.

In one or more exemplary embodiments, displaying graphical representations of the measured surrogate cardiac electrical activation times about the first and second human anatomy portions may include displaying graphical representations of the measured surrogate cardiac electrical activation times about graphical representations of at least one of an anterior side of a heart and a posterior side of a heart.

In one or more exemplary embodiments, displaying the graphical representations of the measured surrogate cardiac electrical activation times about a portion of human anatomy may include color scaling the portions of human anatomy on the graphical user interface according to the measured surrogate cardiac electrical activation times.

One or more exemplary embodiments may further include displaying, on a graphical user interface, at least one electrocardiogram of the patient. Each of the at least one electrocardiogram may be captured using at least one different electrode and may be time-aligned on the graphical user interface.

One exemplary system for assisting in noninvasive evaluation of cardiac therapy may include electrode apparatus (e.g., including a plurality of external electrodes configured to be located proximate tissue of a patient), a display apparatus (e.g., including a graphical user interface configured to present cardiac electrical activation time information and cardiac health information), and computing apparatus coupled to the electrode apparatus and the display apparatus. The computing apparatus may be configured to provide the graphical user interface displayed on the display apparatus. The computing apparatus may be further configured to measure surrogate cardiac electrical activation times using one or more external electrodes of the plurality of external electrodes of the electrode apparatus proximate the patient's heart, measure at least one metric of the patient's cardiac health using one or more external electrodes of the plurality of external electrodes of the electrode apparatus proximate the patient's heart, and allow a user to select one of initial examination mode for assisting a user in noninvasively evaluating the patient for cardiac therapy and follow-up examination mode for assisting a user in noninvasively evaluating cardiac therapy after implantation cardiac therapy. When in initial examination mode, the computing apparatus may be configured to display, on the graphical user interface, a graphical representation of the measured surrogate cardiac electrical activation times about a portion of human anatomy, at least one metric of the patient's cardiac health, and an indication of whether cardiac therapy for the patient may be beneficial. When in follow-up examination mode, the computing apparatus may be configured to display, display, on the graphical user interface, a graphical representation of presently-measured surrogate cardiac electrical activation times about a first human anatomy portion and a graphical representation of previously-measured surrogate cardiac electrical activation times about a second human anatomy portion and at least one presently-measured metric of the patient's cardiac health, at least one previously-measured metric of the patient's cardiac health, and an indication of whether cardiac therapy for the patient appears to be beneficial.

One exemplary a computer-implemented method for assisting in noninvasive evaluation of a patient for cardiac therapy may include measuring surrogate cardiac electrical activation times using one or more external electrodes proximate the patient's heart, measuring at least one metric of the patient's cardiac health using one or more external electrodes proximate the patient's heart, and allowing a user to select one of initial examination mode and follow-up examination mode. The initial examination mode may be configured for assisting a user in noninvasively evaluating the patient for cardiac therapy and the follow-up examination mode may be configured for assisting a user in noninvasively evaluating cardiac therapy after implantation cardiac therapy. When in initial examination mode, the exemplary method display, on a graphical user interface, a graphical representation of the measured surrogate cardiac electrical activation times about a portion of human anatomy, at least one metric of the patient's cardiac health, and an indication of whether cardiac therapy for the patient may be beneficial. When in follow-up examination mode, the exemplary method display, on a graphical user interface, a graphical representation of presently-measured surrogate cardiac electrical activation times about a first human anatomy portion and a graphical representation of previously-measured surrogate cardiac electrical activation times about a second human anatomy portion and at least one presently-measured metric of the patient's cardiac health, at least one previously-measured metric of the patient's cardiac health, and an indication of whether cardiac therapy for the patient appears to be beneficial.

Another exemplary system for assisting in noninvasive evaluation of a patient for cardiac therapy may include means for measuring surrogate cardiac electrical activation times representative of the electrical activation times of a patient's heart, means for measuring at least one metric of the patient's cardiac health, and computing means for allowing a user to select one of initial examination mode and follow-up examination mode. The initial examination mode may be configured for assisting a user in noninvasively evaluating the patient for cardiac therapy and the follow-up examination mode may be configured for assisting a user in noninvasively evaluating cardiac therapy after implantation cardiac therapy. The exemplary system may further include display means for, when in initial examination mode, displaying, on a graphical user interface, a graphical representation of the measured surrogate cardiac electrical activation times about a portion of human anatomy, at least one metric of the patient's cardiac health, and an indication of whether cardiac therapy for the patient may be beneficial, and when in follow-up examination mode, displaying, on a graphical user interface, a graphical representation of presently-measured surrogate cardiac electrical activation times about a first human anatomy portion and a graphical representation of previously-measured surrogate cardiac electrical activation times about a second human anatomy portion and at least one presently-measured metric of the patient's cardiac health, at least one previously-measured metric of the patient's cardiac health, and an indication of whether cardiac therapy for the patient appears to be beneficial.

In one or more exemplary embodiments, a user may be allowed to select an implantation examination mode for assisting a user in noninvasively evaluating cardiac therapy during implantation and configuration of a cardiac therapy. When in implantation examination mode, a graphical representation of presently-measured surrogate cardiac electrical activation times about a first human anatomy portion and a graphical representation of previously-measured surrogate cardiac electrical activation times about a second human anatomy portion and at least one presently-measured metric of the patient's cardiac health, at least one previously-measured metric of the patient's cardiac health, and an indication of whether cardiac therapy for the patient appears to be beneficial may be displayed on a graphical user interface. In at least one embodiment, a user may be allowed to change at least one pacing parameter of an implantable medical device providing cardiac therapy to the patient.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
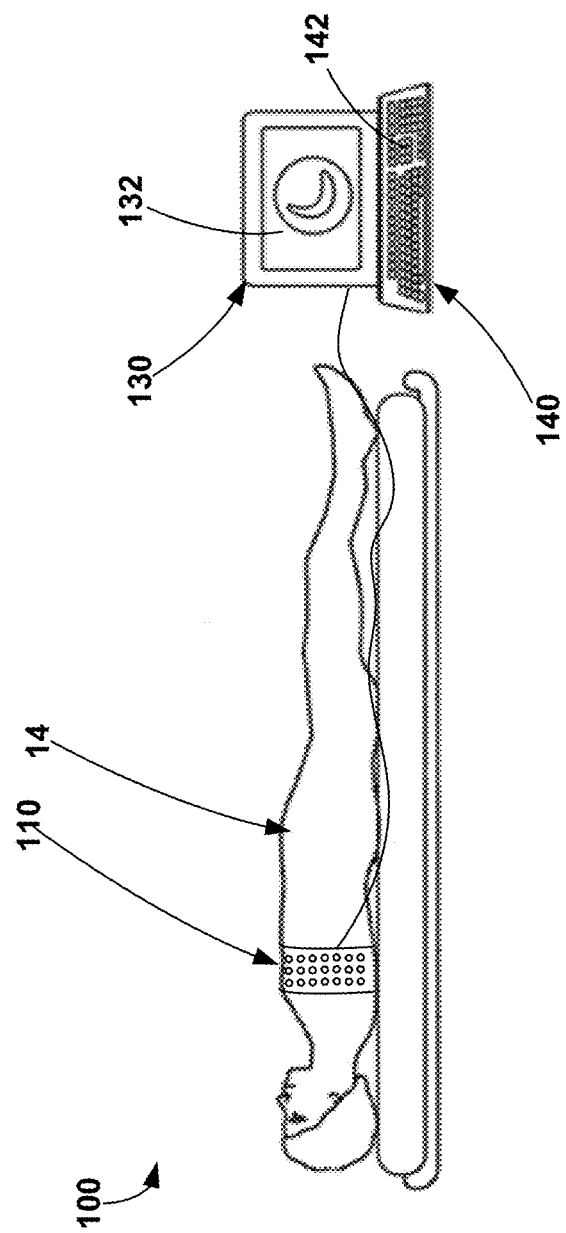
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems, apparatus, and methods shall be described with reference to FIGS. 1-11. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

From unipolar electrocardiogram (ECG) recordings, cardiac electrical activation times can be detected or estimated in proximity of a reference location (e.g., which can be a chosen location for the left ventricle lead during implant). Such electrical activation times may be measured and displayed, or conveyed, to an implanter by a system which acquires the ECG signals and generates the metric of electrical activation times (e.g., depolarization) measured from various ECG locations. As described herein, at least in one or more embodiments, electrical activation times displayed on a graphical user interface may be used in noninvasive evaluation of a patient for cardiac therapy and/or evaluation of cardiac therapy.

Various exemplary systems, methods, and interfaces may be configured to use electrode apparatus including external electrodes, display apparatus, and computing apparatus to noninvasively assist a user (e.g., a physician) in the evaluation of a patient for cardiac therapy and/or evaluation of cardiac therapy. An exemplary system 100 including electrode apparatus 110, display apparatus 130, and computing apparatus 140 is depicted in FIG. 1.

The electrode apparatus 110 as shown includes a plurality of electrodes incorporated, or included within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis. Exemplary electrode apparatus may be described in U.S. Provisional Patent Application 61/913,759 entitled "Bioelectric Sensor Device and Methods" and filed on Dec. 9, 2013 and U.S. patent application Ser. No. entitled "Bioelectric Sensor Device and Methods" and filed on even date herewith, each of which is incorporated herein by reference in its entirety. Further, exemplary electrode apparatus 110 will be described in more detail in reference to FIGS. 2A-2B.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of at least a portion of the patient except noninvasive tools such as contrast solution. It is to be understood that the exemplary systems, methods, and interfaces described herein may noninvasively assist a user (e.g., a physician) in evaluation of a patient for cardiac therapy and/or on-going cardiac therapy delivered to a patient, and after the exemplary systems, methods, and interfaces have provided the noninvasive assistance, the exemplary systems, methods, and interfaces may then provide assistance to implant, or navigate, an implantable electrode into the patient, e.g., proximate the patient's heart, using imaging apparatus.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body. Exemplary systems and methods that use imaging apparatus and/or electrode apparatus may be described in U.S. patent application Ser. No. 13/916,353 filed on Jun. 12, 2013 and entitled "Implantable Electrode Location Selection," U.S. patent application Ser. No. 13/916,377 filed on Jun. 12, 2013 and entitled "Implantable Electrode Location Selection," U.S. Provisional Patent Application No. 61/817,483 filed on Apr. 30, 2013 and entitled "Identifying Effective Electrodes," U.S. Provisional Patent Application 61/817,480 filed on Apr. 30, 2013 and entitled "Identifying Optical Electrical Vectors," U.S. Provisional Patent Application 61/913,795 entitled "Systems, Methods, and Interfaces for Identifying Effective Electrodes" and filed on Dec. 9, 2013, U.S. patent application Ser. No. 14/227,955 entitled "Systems, Methods, and Interfaces for Identifying Effective Electrodes" and filed on Mar. 27, 2014, U.S. Provisional Patent Application 61/913,784 entitled "Systems, Methods, and Interfaces for Identifying Optimal Electrical Vectors" and filed on Dec. 9, 2013, and U.S. patent application Ser. No. 14/227,919 entitled "Systems, Methods, and Interfaces for Identifying Optimal Electrical Vectors" and filed on Mar. 27, 2014, each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus may be configured to capture a plurality of consecutive images (e.g., continuously) to provide video frame data. In other words, a plurality of images taken over time using the imaging apparatus may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

Examples of systems and/or imaging apparatus may be described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which are incorporated herein by reference in their entireties.

The display apparatus 130 and the computing apparatus 140 may be configured to display and analyze data such as, e.g., surrogate electrical activation information or data, electrocardiogram data, etc. gathered, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in location selection of an implantable electrode, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 to view and/or select one or more pieces of information related to a patient's cardiac health as further described herein.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including graphical depictions of anatomy of a human heart, images or graphical depictions of the patient's heart, graphical depictions of locations of one or more electrodes, graphical depictions of a human torso, images or graphical depictions of the patient's torso, alphanumeric representations of one or more values, graphical depictions or actual images of implanted electrodes and/or leads, etc. For example, the display apparatus 130 may include a liquid crystal display, an organic light-emitting diode screen, a touchscreen, a cathode ray tube display, etc.

The graphical user interfaces 132 displayed by the display apparatus 130 may include, or display, one or more regions used to display graphical depictions, to display images, to allow selection of one or more regions or areas of such graphical depictions and images, etc. As used herein, a "region" of a graphical user interface 132 may be defined as a portion of the graphical user interface 132 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 132 may be defined as a portion of the graphical user interface 132 located with a region that is smaller than the region it is located within.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, mini computer, tablet computer, etc.). The exact configuration of the computing apparatus 130 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2A:
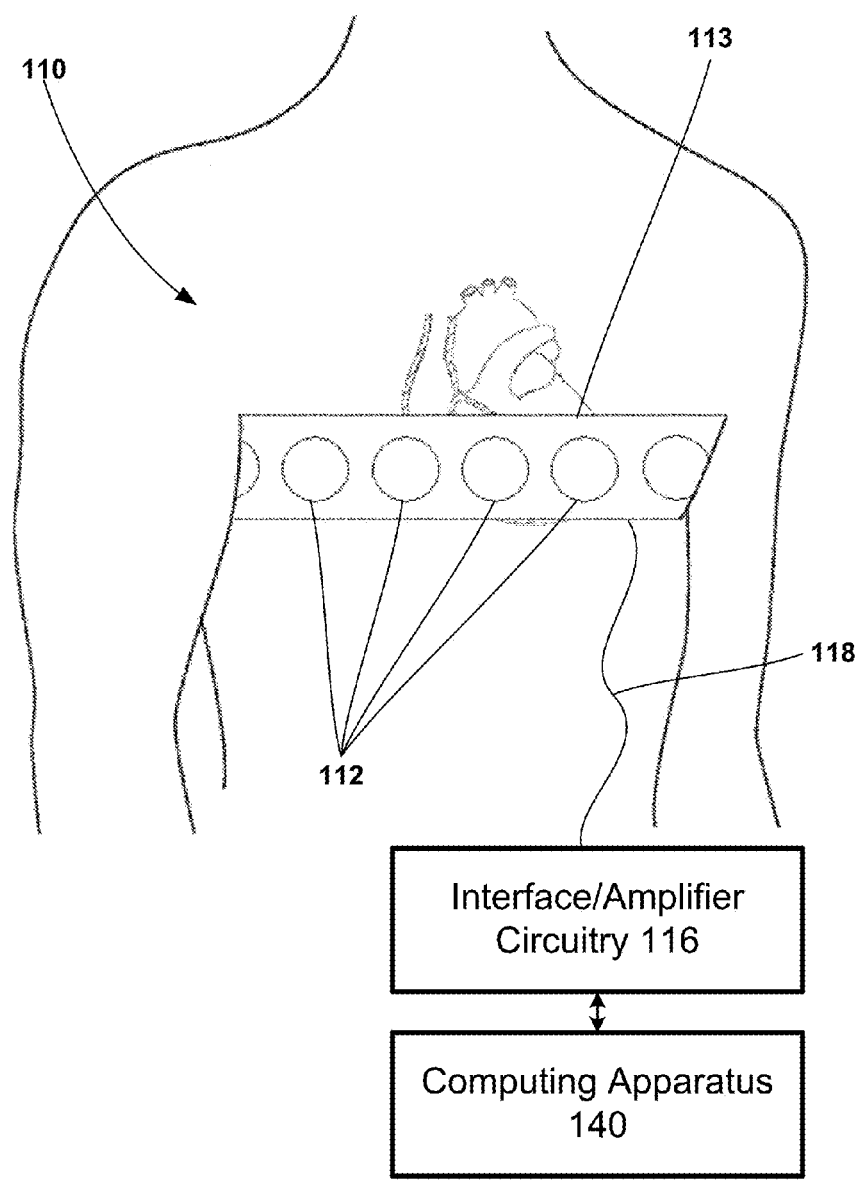
FIGS. 2A-2B are diagrams of exemplary external electrode apparatus for measuring torso-surface potentials.

The electrical activation times of the patient's heart may be useful to evaluate a patient's cardiac health and/or to evaluate cardiac therapy being delivered to a patient. Electrical activation information or data of one or more regions of a patient's heart may be determined using electrode apparatus 110 as shown in FIG. 1 and in FIGS. 2A-2B. The exemplary electrode apparatus 110 may be configured to measure body-surface potentials of a patient 14 and, more particularly, torso-surface potentials of a patient 14. As shown in FIG. 2A, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2A the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14. Still further, in other examples, the electrodes 112 may be part of, or located within, two sections of material or two "patches." One of the two sections or patches may be located on the anterior side of the torso of the patient 14 (to, e.g., measure surrogate cardiac electrical activation times representative of the anterior side of the patient's heart) and the other section or patch may be located on the posterior side of the torso of the patient 14 (to, e.g., measure surrogate cardiac electrical activation times representative of the posterior side of the patient's heart).

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide surrogate electrical activation information or data such as surrogate cardiac electrical activation times, e.g., representative of actual, or local, electrical activation times of one or more regions of the patient's heart as will be further described herein. For example, electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring time between the onset of cardiac depolarization (e.g., onset of QRS complex) to the next the onset of cardiac depolarization. In one or more embodiments, measurement of activation times can be performed by picking an appropriate fiducial point (e.g., peak values, minimum values, minimum slopes, maximum slopes, zero crossings, threshold crossings, etc. of a near or far-field EGM) and measuring time between fiducial points (e.g., within the electrical activity).

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a patient for cardiac therapy and/or evaluate cardiac therapy being delivered to the patient.

Figure 2B:
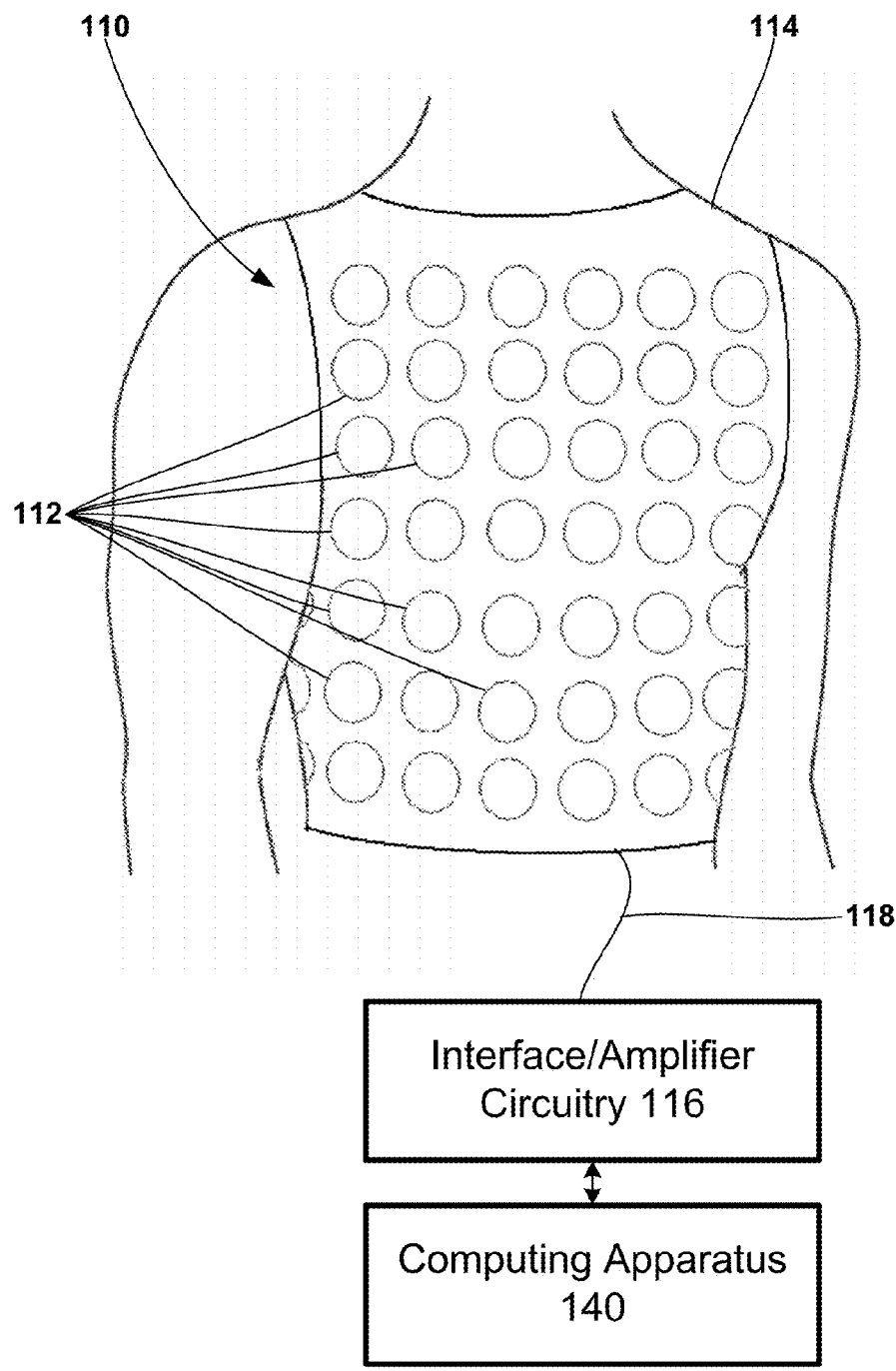

FIG. 2B illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2A, the electrode apparatus 110 of FIG. 2B may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the anterior, lateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

As described herein, the electrode apparatus 110 may be configured to measure electrical information (e.g., electrical signals) representing different regions of a patient's heart. More specifically, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces may be used in one or more different settings to provide noninvasive assistance to a user in the evaluation of a patient for cardiac therapy and/or evaluation of on-going cardiac therapy (e.g., cardiac therapy being presently-delivered to a patient). Further, the exemplary systems, methods, and interfaces may be used to assist a user in the configuration and/or adjustment of one or more cardiac therapy settings for the cardiac therapy to be delivered to a patient or being presently-delivered to a patient.

Figure 3:
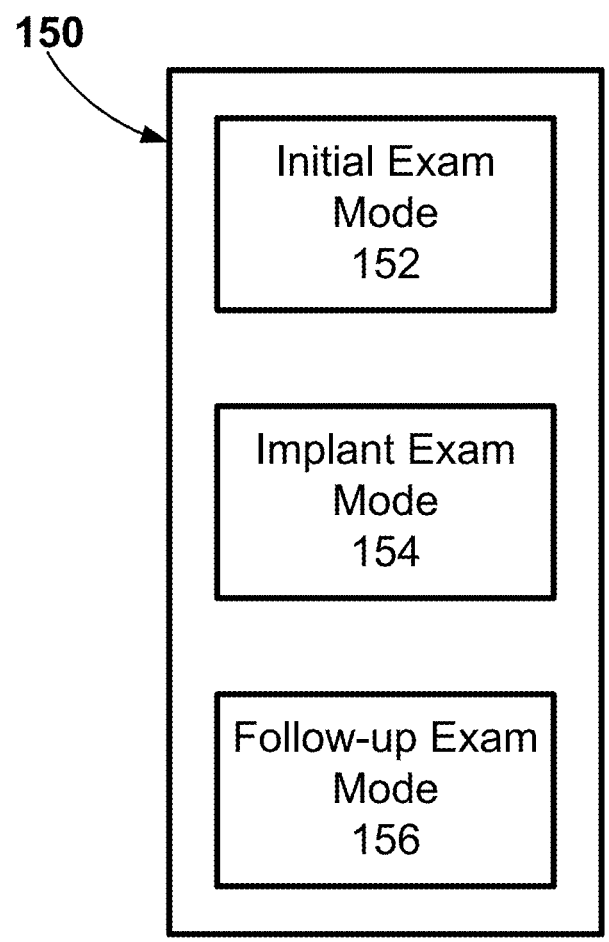
FIG. 3 is a block diagram of exemplary modes for noninvasive cardiac evaluation.

To provide this functionality, the exemplary systems, methods, and interfaces may be described as being configurable in a plurality of modes of operation 150 as depicted in FIG. 3. For example, the exemplary systems, methods, and interfaces may be configured in an initial examination mode 152, an implantation examination mode 154, and a follow-up examination mode 156.

The initial examination mode 152 may be configured for the noninvasive evaluation of a patient for cardiac therapy. For example, the initial examination mode 152 may be designed for an initial consultation/evaluation of a patient considering cardiac therapy and will be described further herein in reference to the exemplary initial examination graphical user interface of FIG. 4.

The implantation examination mode 154 may be configured for the noninvasive evaluation of cardiac therapy being delivered to a patient and/or being currently configured for a patient (e.g., during configuration of cardiac resynchronization therapy (CRT) after implantation of the CRT device). For example, the implantation examination mode 154 may be designed for use by a physician in evaluating cardiac therapy during implantation of a cardiac therapy device, immediately after implantation of a cardiac therapy device and/or during configuration of the cardiac therapy immediately following implantation. Further, exemplary systems configurable in the implantation examination mode 154 may include additional functionality such as imaging and navigation functionality for electrode and/or lead placement as described herein. The implantation examination mode 154 will be described further herein in reference to the exemplary implantation examination graphical user interface of FIG. 6.

The follow-up examination mode 156 may be configured for the noninvasive evaluation of cardiac therapy being delivered to a patient after a cardiac therapy device has been delivering cardiac therapy to a patient for a period of time (e.g., after implantation, not immediately following implantation or initial configuration of the cardiac therapy, etc.). For example, the follow-up examination mode 156 may be designed for use by a physician in evaluating cardiac therapy in follow-up appointments days, weeks, months, or years after a cardiac therapy has been implanted in a patient and will be described further herein in reference to the exemplary follow-up examination graphical user interface of FIG. 8.

The exemplary systems, methods, and interfaces may provide, or be configurable in, one or more of the plurality of modes 150. For example, an exemplary system may provide, or be configurable in, all of the plurality of modes 150. Further, for example, an exemplary system may provide, or be configurable in, two of the three modes 150 such as, e.g., the initial examination mode 152 and the follow-up mode 156. In at least one embodiment, a system designed for use in an operating room of a medical care facility (e.g., for the surgical implantation and configuration of a cardiac therapy device) may include each of the three modes 150. In at least one embodiment, a system designed for use in a consultation room of a medical care facility (e.g., for general evaluation and consultation of a patient) may include the initial examination mode 152 and the follow-up mode 156 but not the implantation mode 154.

Figure 4:
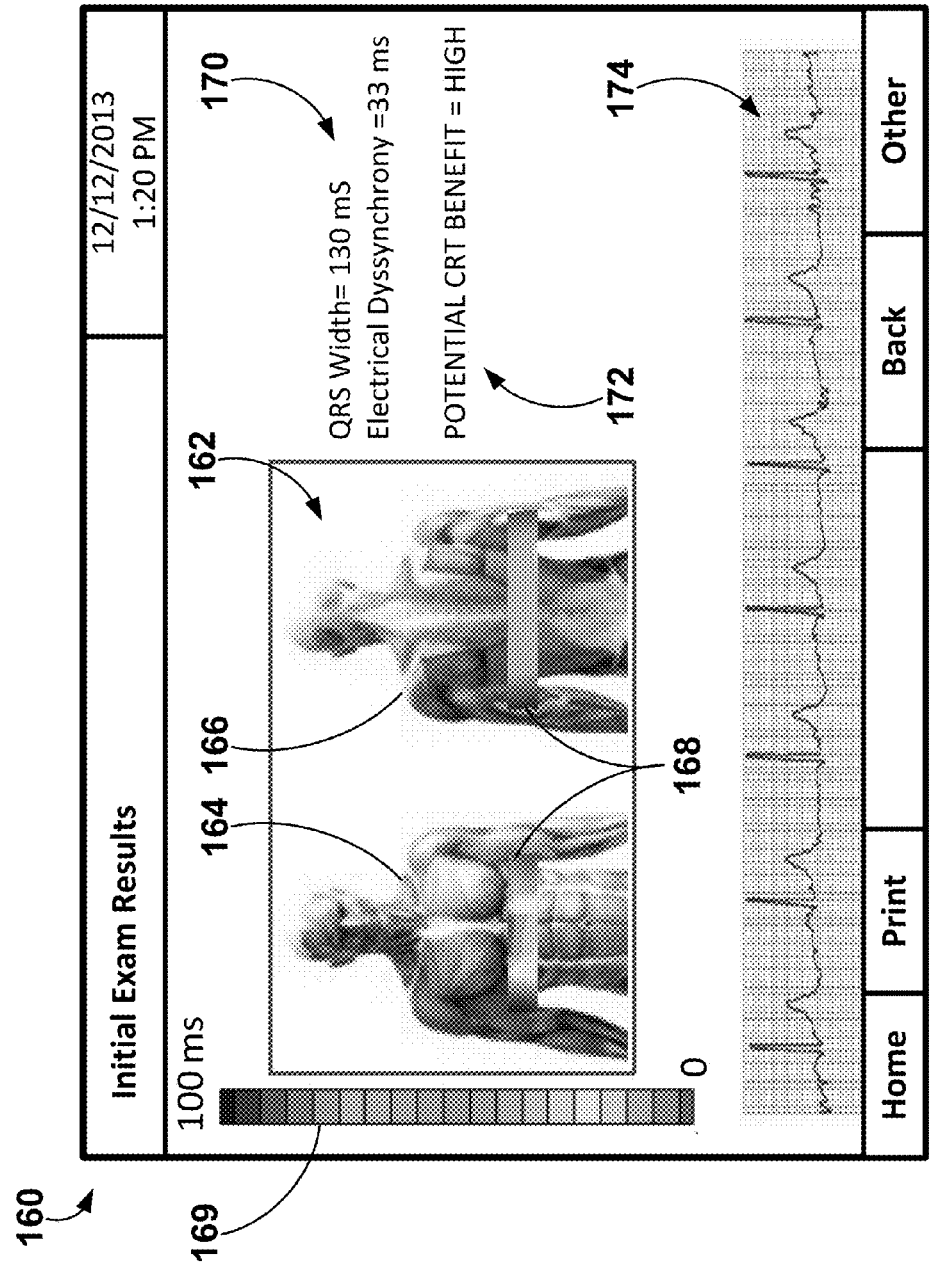
FIG. 4 is an exemplary initial examination graphical user interface depicting electrical activation information, cardiac health metrics, and an indication of the benefit of cardiac therapy.

An exemplary graphical interface (GUI) 160 for use in an initial examination or consultation is depicted in FIG. 4. As shown, the GUI 160 may include, among other things, a graphical representation 162 of measured surrogate electrical activation times, metrics 170 of cardiac health, and an indication 172 of whether cardiac therapy for the patient may be beneficial. The initial examination may include applying electrode apparatus such as described herein with reference to FIGS. 1-2 to a patient, measuring surrogate electrical activation times and ECG information using the electrode apparatus, and displaying the data for the evaluation of the patient for cardiac therapy on the GUI 160.

The graphical representation 162 of measured surrogate cardiac electrical activation times may be depicted in a variety of fashions. As shown, the surrogate electrical activation times are shown as a color-coded, or color-scaled, segment 168 extending over, or wrapped around, a graphical representation of a human torso 164, 166. More specifically, an anterior side of a human torso 164 and a posterior side of a human torso 166 are depicted, each including a color-coded segment 168 graphically depicting surrogate electrical activation times measured, e.g., using the electrical apparatus described herein with reference to FIGS. 1-2. Further, the graphical representation 162 of measured surrogate cardiac electrical activation times shown on the anterior side of a human torso 164 may be measured using electrodes located on, or proximate to, the anterior side of the patient's torso, and likewise, the graphical representation 162 of measured surrogate cardiac electrical activation times shown on the posterior side of the human torso 166 may be measured using electrodes located on, or proximate to, the posterior side of the patient's torso. In other words, the graphical representation 162 of measured surrogate cardiac electrical activation times shown on the anterior side of the human torso 164 correlates to actual electrical signals measured using electrodes configured to measure electrical signals on the anterior side of the patient's torso, and the graphical representation 162 of measured surrogate cardiac electrical activation times shown on the posterior side of the human torso 166 correlates to actual electrical signals measured using electrodes configured to measure electrical signals on the posterior side of the patient's torso. The graphical representation 162 further includes a color-coded scale 169 corresponding to the color-coded segments 168, to, e.g., provide basis for the coloring of the color-coded segments 168.

Additional exemplary graphical representations of surrogate electrical activation times may be described in U.S. Patent Application Publication No. 2012/0284003 A1 published on Nov. 8, 2012 and entitled "Assessing Intra-Cardiac Activation Patterns" and U.S. Patent Application Publication No. 2012/0283587 A1 published on Nov. 8, 2012 and entitled "Assessing Intra-Cardiac Activation Patterns and Electrical Dyssynchrony," each of which are hereby incorporated by reference in their entireties.

In other embodiments, the surrogate electrical activation times may be color-coded across the entire graphical depiction of a human torso and/or any smaller or larger part of human anatomy. Further, in at least one embodiment, the graphical depictions of a human torso 164, 166 may be actual images of the patient being evaluated. The surrogate cardiac electrical activation times may be further depicted alphanumerically over a graphical depiction of human anatomy. For example, a plurality of surrogate cardiac electrical activation times in milliseconds may be graphically overlaid over the torsos 164, 166.

Figure 5:
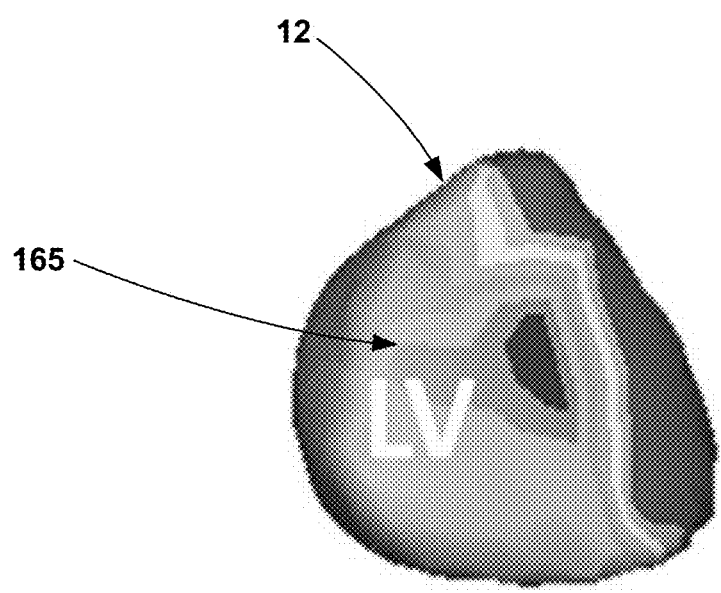
FIG. 5 is a graphical representation of a human heart including activation times mapped thereon.

In one or more embodiments, the graphical depiction of a portion of human anatomy displayed on the exemplary graphical user interfaces may include a graphical representation of a human heart. For example, a posterior side of a human heart 12 is depicted in FIG. 5 with surrogate electrical activation times color-coded across the surface of the heart 12. As shown, the posterolateral left ventricle region 165 shows late activation (e.g., about 150 milliseconds). In other embodiments, both a posterior and anterior side of a human heart may be graphically depicted and overlaid with electrical activation information.

The exemplary GUI 160 of FIG. 4 further includes metrics 170 of the patient's cardiac health. As shown, the metrics 170 are QRS width and electrical dyssynchrony, which both may be useful in the evaluation of the patient for cardiac therapy. Although in this embodiment, the metrics 170 include two metrics, it is to be understood that exemplary graphical user interfaces may include one metric or more than two metrics related to the patient's cardiac health. For example, the metrics 170 may include one or more of a standard deviation, range, interquartile deviation, one or more statistical averages (e.g., mean, median, mode) of activation times of all electrodes or a subset of electrodes proximate a specific portion of anatomy (such as, e.g., electrodes located at the left side of the patient that are surrogate of the left ventricle), one or more timing intervals between certain fiducial points (e.g., onset of depolarization to first negative or positive peak on one or more electrocardiograms, etc.), etc. Further, the cardiac health metrics may include one or more metrics described in U.S. Provisional Patent Application No. 61/834,133 entitled "METRICS OF ELECTRICAL DYSSYNCHRONY AND ELECTRICAL ACTIVATION PATTERNS FROM SURFACE ECG ELECTRODES" and filed on Jun. 12, 2013, which is hereby incorporated by reference it its entirety The exemplary GUI 160 of FIG. 4 further includes an indication 172 of whether cardiac therapy for the patient may be beneficial. The indication 172 of whether cardiac therapy for the patient may be beneficial may be defined as a suggestion or recommendation based on the measured electrical data from the electrode apparatus with respect to a potential cardiac therapy. In the exemplary GUI 160, the indication 172 of whether cardiac therapy for the patient may be beneficial notes the following: "POTENTIAL CRT BENEFIT=HIGH," and thus, the indication 172 indicates that this patient may have a high likelihood of benefiting from cardiac resynchronization therapy.

Additionally, the exemplary GUI 160 of FIG. 4 includes an electrocardiogram area 174 that depicts one or more electrocardiograms of the patient measured using the electrode apparatus. Although only one electrocardiogram is depicted in the electrocardiogram area 174, a plurality of electrocardiograms may be depicted in the electrocardiogram area 174 and/or other areas of the GUI 160. Further, one or more (e.g., a set or subset) of available electrocardiograms (e.g., measured using different electrodes or electrode sets located in different locations about a patient) may be selected by a user (e.g., physician) for viewing on the GUI 160. When the electrocardiogram area 174 includes more than one electrocardiogram, the electrocardiograms may be time-aligned (e.g., the electrograms may be aligned along the same time period, the electrograms may be aligned by cardiac cycle, etc.). Additionally, each electrogram may cover either a single beat or multiple beats, which may be selected or configured by a user. Further, the one or more electrocardiograms may be stored from a previous examination such that a user may compare previously-recorded electrocardiograms to presently-monitored electrocardiograms.

The data such as electrical activation time data, metrics of cardiac health, electrocardiograms, etc. measured when using the initial examination mode may be stored within the computing apparatus for use at a later time, e.g., to compare the patient's cardiac health before cardiac therapy to after cardiac therapy, to adjust or configure cardiac therapy for a patient, etc. For example, the data collected during the initial examination/consultation depicted in the initial examination graphical user interface 160 of FIG. 4 is used in the exemplary implantation graphical user interface 180 of FIG. 6 and the exemplary follow-up graphical user interface 220 of FIG. 8.

Figure 6:
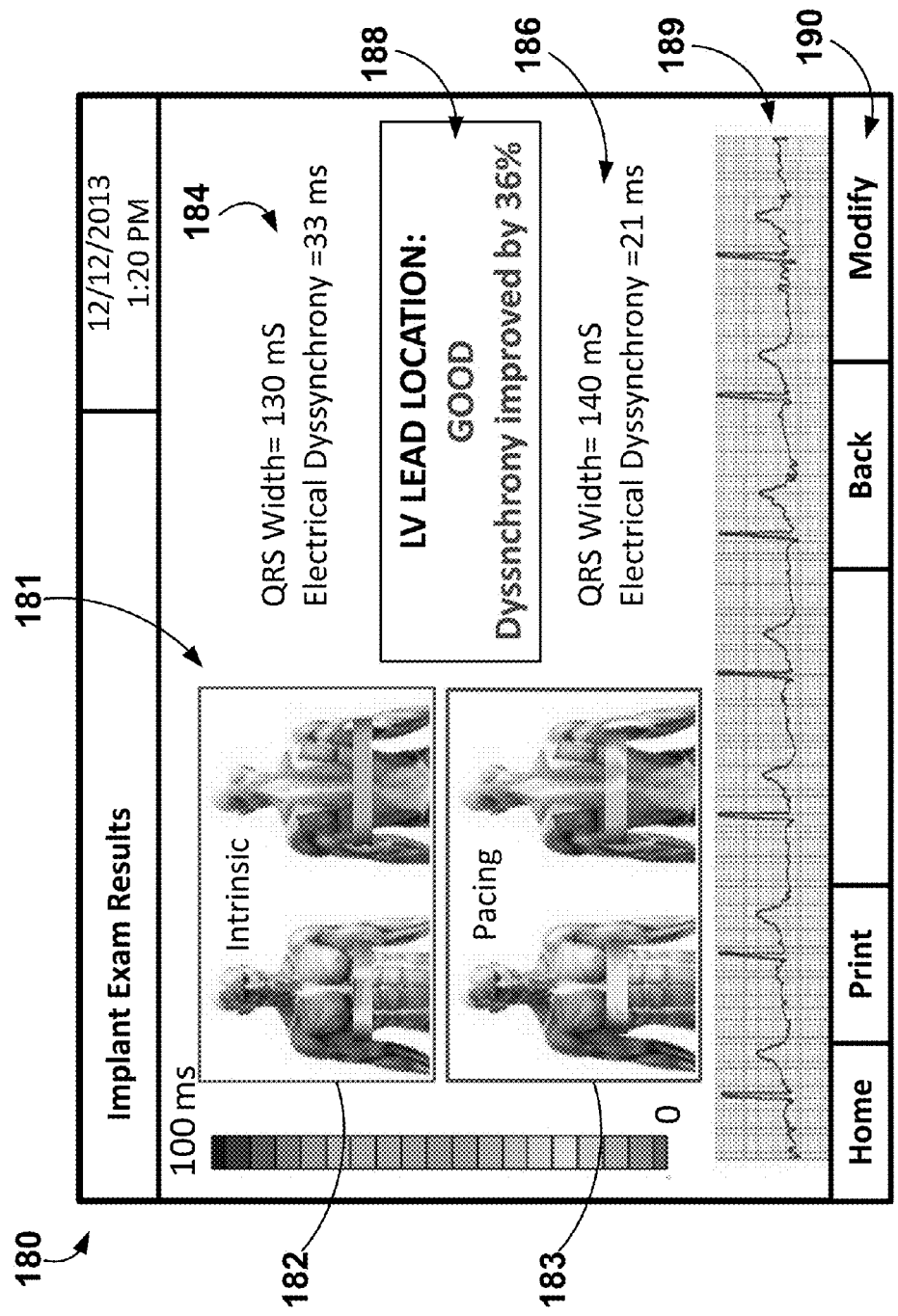
FIG. 6 is an exemplary implant examination graphical user interface depicting previously- and presently-measured electrical activation information and cardiac health metrics.

During implantation of a cardiac therapy device such, e.g., as a cardiac resynchronization therapy device, the exemplary systems, methods, and interfaces may be configured to provide noninvasive evaluation of the cardiac therapy being implanted. An exemplary graphical interface (GUI) 180 for use during implantation is depicted in FIG. 6. As shown, the GUI 180 may include, among other things, graphical representations 181 of previously-measured and presently measured surrogate electrical activation times, previously-measured and presently-measured metrics 184, 186 of cardiac health, and an indication 188 of whether the cardiac therapy appears to be beneficial. Although the surrogate electrical activation times and cardiac health metrics are described as being previously-measured or presently-measured, it is to be understood that "previously-measured" data is designed to encompass, or describe, any measurements prior to the "presently-measured" data, and, likewise, "presently-measured" data is designed to encompass, or describe, any measurements after to the "previously-measured" data. In one or more embodiments, the "previously-measured" data may represent data measured during intrinsic rhythm before cardiac therapy (e.g., implantation of a CRT device). In other words, the "previously-measured" data may represent baseline values. In one or more embodiments, the "previously-measured" data may represent data measured with cardiac therapy being disabled or before any adjustments or modifications are made to cardiac therapy being presently delivered (e.g., by CRT device) and the "presently-measured" data may represent data measured after the adjustments or modifications are made.

Similar to the initial examination, electrode apparatus such as described herein with reference to FIGS. 1-2 may be applied to a patient, surrogate electrical activation times and ECG information using the electrode apparatus may be measured, and the surrogate electrical activation times and ECG information data may be displayed on the GUI 180. In at least one embodiment, the GUI 180 may be described as providing a before-and-after representation of the cardiac health of a patient before cardiac therapy and after cardiac therapy.

The graphical representations 181 of previously-measured and presently measured surrogate electrical activation times include a graphical representation 182 of previously-measured surrogate electrical activation times and a graphical representation 183 of presently-measured surrogate electrical activation times. As labeled on the GUI 180, the graphical representation 182 of previously-measured surrogate electrical activation times represents the patient's intrinsic rhythm (e.g., without pacing, without cardiac therapy, etc.) and the graphical representation 183 of presently-measured surrogate electrical activation times represents the patient's paced rhythm. The graphical representations 182, 183 may be substantially similar to the graphical representation 162 of the GUI 160 described herein with reference to FIG. 4.

The GUI 180 further includes previously-measured metrics 184 of cardiac health and presently-measured metrics 186 of cardiac health for the patient such that a user may compare the values presented thereby to, e.g., evaluate the cardiac therapy being delivered. As shown, similar to the initial examination GUI 160, the metrics 184, 186 include QRS width and electrical dyssynchrony. As shown, the QRS width has increased by 10 milliseconds and the electrical dyssynchrony has decreased 12 milliseconds from the intrinsic data to the paced data, which may, e.g., indicate that the cardiac therapy being delivered to the patient is beneficial. The GUI 180 further includes an indication 188 of whether the cardiac therapy appears to be beneficial. In this example, the indication 188 notes: "LV LEAD LOCATION: GOOD Dyssynchrony improved by 36%." Although this indication 188 is based on an electrical dyssynchrony comparison between the previously-measured electrical dyssynchrony, other exemplary indications of whether cardiac therapy appears to be beneficial for a patient may include, or utilize, different data such as, e.g., comparisons of ECG waveform between previously measured ECG waveform shape (e.g., as may be described in "Analysis of Ventricular Activation Using Surface Electrocardiography to Predict Left Ventricular Reverse Volumetric Remodeling During Cardiac Resynchronization Therapy" by Sweeney, et al., *Circulation: Arrhythmia/Electrophysiology*, Feb. 9, 2010: pages 626-634, which is incorporated herein by reference in its entirety), changes in ECG vector loop areas (e.g., as may be described in "Vectorcardiography as a Tool for Easy Optimization of Cardiac Resynchronization Therapy in Canine Left Bundle Branch Block Hearts" by van Deursen et al., *Circulation: Arrhythmia/Electrophysiology*, June 2012: pages 544-552, which is incorporated herein by reference in its entirety), changes in QRS duration, etc.

Additionally, the GUI 180 of FIG. 6 may include an electrocardiogram area 189 similar to the electrocardiogram area 174 described herein with reference to FIG. 4. Further, the electrocardiogram area 189 may include one or more presently- and/or previously-measured electrocardiograms, which may be selected by a user. When the electrocardiogram area 189 includes more than one electrocardiogram, the electrocardiograms may be time-aligned as described herein.

A user (e.g., a physician) may use the GUI 180 during implantation of a cardiac therapy device and/or in the configuration of the cardiac therapy device. For example, the user may use the GUI 180 to confirm that the implanted cardiac therapy device (e.g., cardiac resynchronization therapy device) is providing beneficial therapy to the patient. Additionally, the user may want to change one or more settings of configurations of the cardiac therapy device while actively monitoring whether the cardiac therapy is beneficial to the patient. For example, the user may want to change a pacing timing interval, change a pacing vector, and/or change a pacing mode while actively monitoring the cardiac therapy using the GUI 180.

Figure 7:
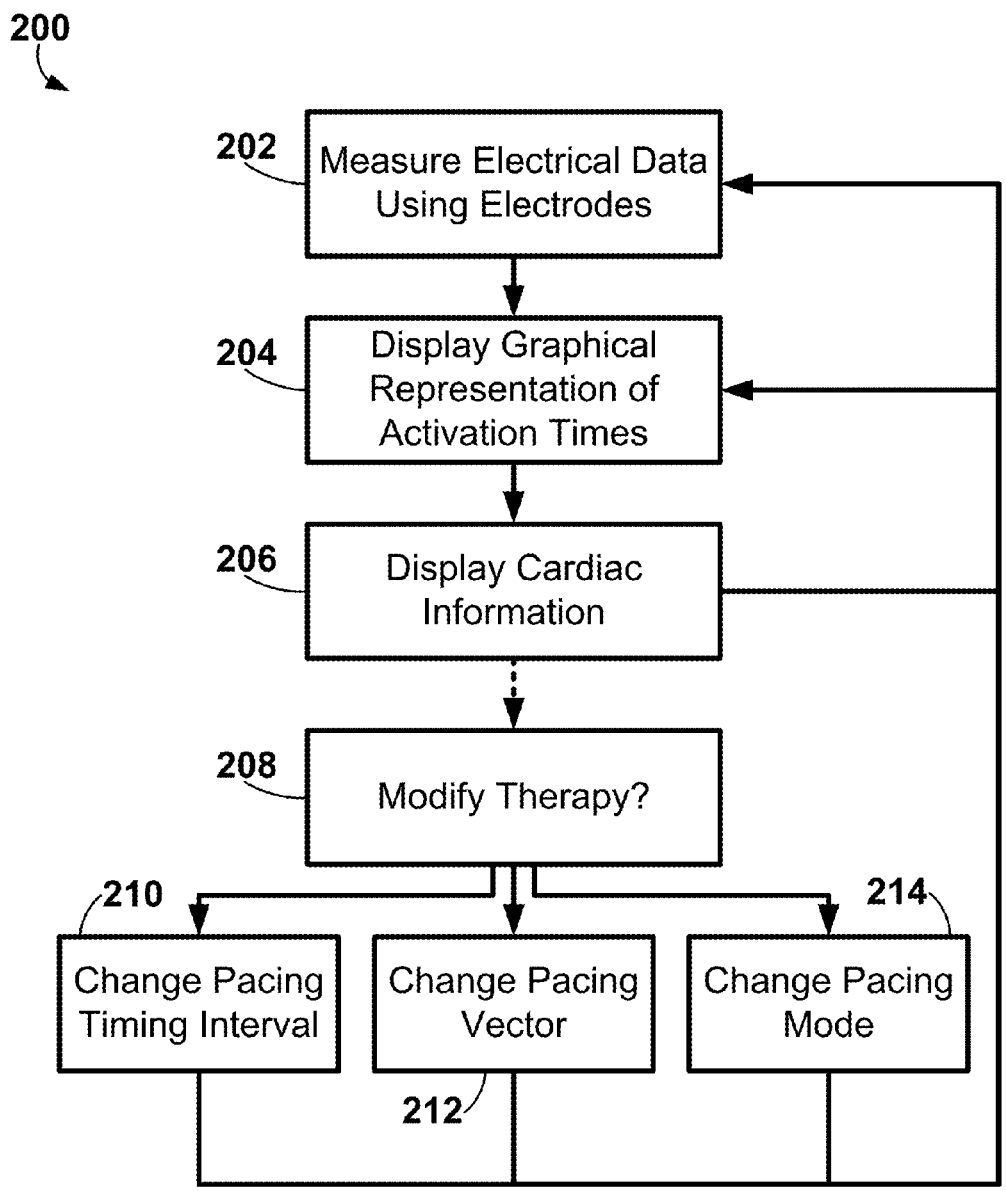
FIG. 7 is a block diagram of an exemplary method of noninvasive evaluation of cardiac therapy for a patient and configuration cardiac therapy.

An exemplary method of noninvasive evaluation of cardiac therapy for a patient and configuration of cardiac therapy 200 using, e.g., GUI 180 of FIG. 6, is depicted in FIG. 7. As shown, the method 200 may measure electrical data using electrode apparatus 202 such as, e.g., electrical activation times, electrocardiograms, etc. The electrical activation times may be displayed 204 on the GUI 180 such as the graphical depictions/representations of surrogate electrical activation times about a human anatomy portion. Further, the cardiac information/metrics based on the measured electrical data may also be displayed 206 on the GUI 180 such as electrical dyssynchrony.

Based on the information displayed by the GUI 180, a user may decide to modify the cardiac therapy 208. In at least one embodiment, the GUI 180 may provide the interface to modify/program the cardiac therapy device (e.g., modify or adjust one or more various configurations, parameters, etc. of the cardiac therapy device). For example, as shown in FIG. 6, the GUI 180 may include a modify area, or button, 190 that, upon selection, may trigger or initiate another graphical user interface used to modify or program the cardiac therapy device.

As described herein, a user may want to change a pacing timing interval 210, change a pacing vector 212, and/or change a pacing mode 214. The timing intervals may include A-V intervals, V-V intervals, etc. for two, three, and/or four chambers of the heart (e.g., two or more of the right atrium, the right ventricle, the left atrium, and the left ventricle) and/or timing intervals for multiple pulses delivered for a single cardiac cycle to the right and left ventricle from different electrodes (e.g. RV electrode to LV1 electrode, LV1 electrode to LV2 electrode, etc.). Changing the pacing vector 212 may include changing one or more electrodes that may be used for various pacing vectors during the programmed therapy. For example, one electrode of a pacing vector may be switched from a tip electrode to ring electrode. Further, any of one or more pacing electrodes (e.g., electrodes located on leads, leadless/wireless electrodes, etc.) used in cardiac therapy systems may be selected or changed for any pacing vector. Changing the pacing mode 214 may include changing the type of pacing being provided. For example, a cardiac therapy device may be delivering LV-only pacing, and a user may switch the LV-only pacing to bi-ventricular pacing. Similarly, a pacing configuration may be changed to pace from a single location within one chamber of the heart to pacing more than two or more locations within that same chamber with or without programmed timing delays.

After the user has adjusted or modified the cardiac therapy, the graphical depiction 183 of the presently-measured activation times and the presently-measured metrics 186 may be updated to reflect the results from the new adjustments or modifications to the cardiac therapy. Thus, a user may immediately know whether any adjustments or modifications have appeared to benefit the patient.

Further, although the graphical depiction 182 of the previously-measured activation times and the previously-measured cardiac metrics 184 of the GUI 180 depicted in FIG. 6 show measurements from intrinsic rhythm, the GUI 180 could be configured (e.g., by user selection, etc.) to show previously-measured data that was measured or recorded prior to any adjustments or modifications being made to the cardiac therapy. Still further, the indication 188 of whether the cardiac therapy appears to be beneficial may also be updated to reflect the change.

Figure 8:
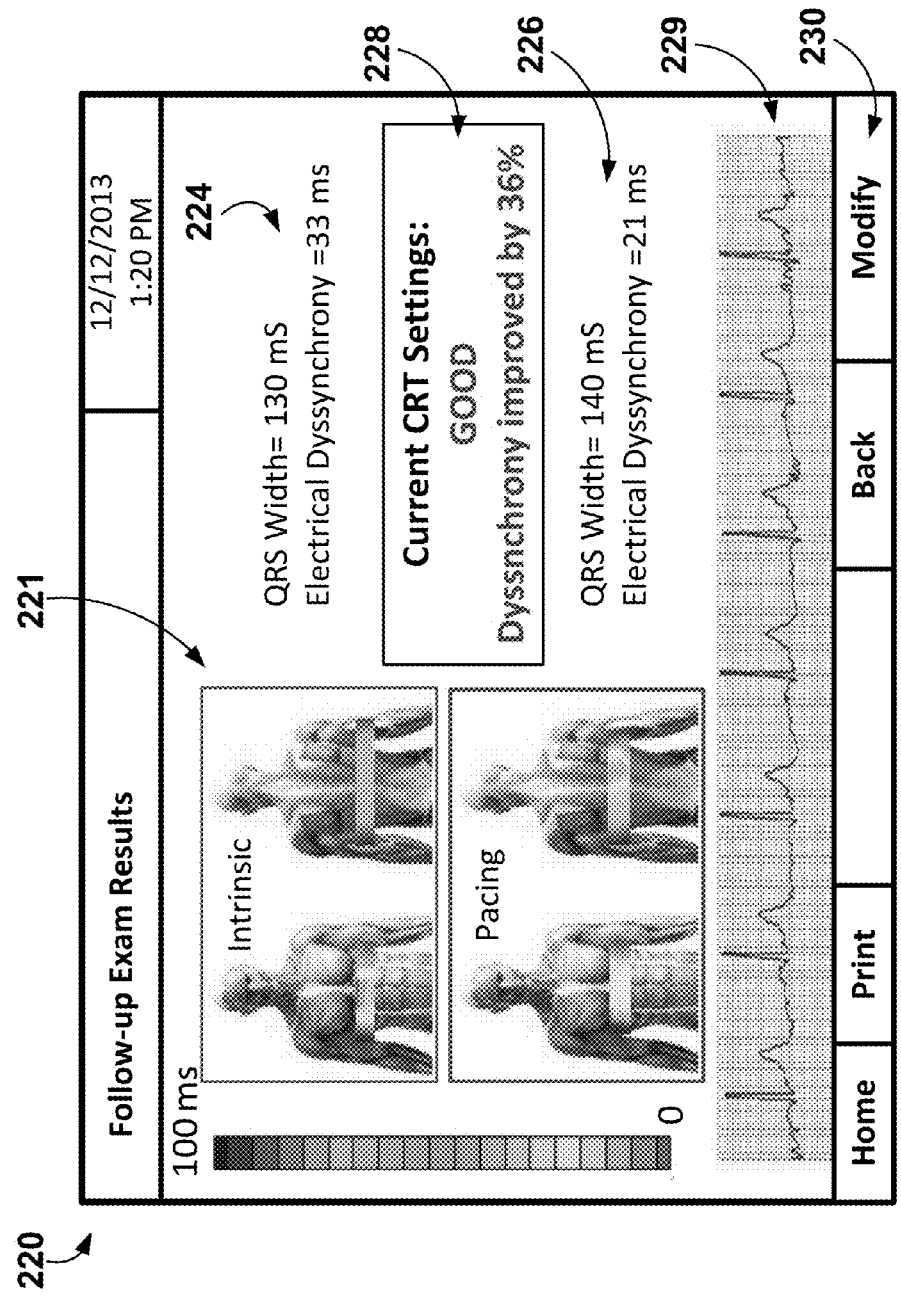
FIG. 8 is an exemplary follow-up examination graphical user interface depicting previously- and presently-measured electrical activation information and cardiac health metrics.

After implantation of a cardiac therapy device such, e.g., as a cardiac resynchronization therapy device, the exemplary systems, methods, and interfaces may be configured to provide noninvasive evaluation of the cardiac therapy after implantation (e.g., days, weeks, months, years, etc. after implantation). An exemplary graphical interface (GUI) 220 for use during a follow-up examination is depicted in FIG. 8. As shown, the GUI 220 may include graphical representations 221 of previously-measured and presently measured surrogate electrical activation times, previously-measured and presently-measured metrics 224, 226 of cardiac health, an indication 228 of whether the cardiac therapy appears to be beneficial, electrocardiogram area 229, and a modify area/button 230 that may be substantially similar to the graphical representations 181, previously-measured and presently measured metrics 184, 186, an indication 188, and electrocardiogram area 189, and modify area/button 190 of the GUI 180 described herein with respect to FIG. 6. The electrocardiogram area 189 may be configured to depict a plurality of different electrocardiograms (e.g., time-aligned, etc.). For example, the electrocardiogram area 189 may display electrocardiographic waveform data, such as several time-aligned single- or multiple beat electrocardiographic waveforms from the same cardiac cycle(s) measured from different electrode(s) around the patient's torso, which may be selected by a user.

The implantable electrodes that may be implanted using the exemplary systems, methods, and graphical user interfaces described herein may be used with respect to the implantation and configuration an implantable medical device (IMD) and/or one or more leads configured to be located proximate one or more portions of a patient's heart. For example, the exemplary systems, methods, and interfaces may be used in conjunction with an exemplary therapy system 10 described herein with reference to FIGS. 9-11.

Figure 9:
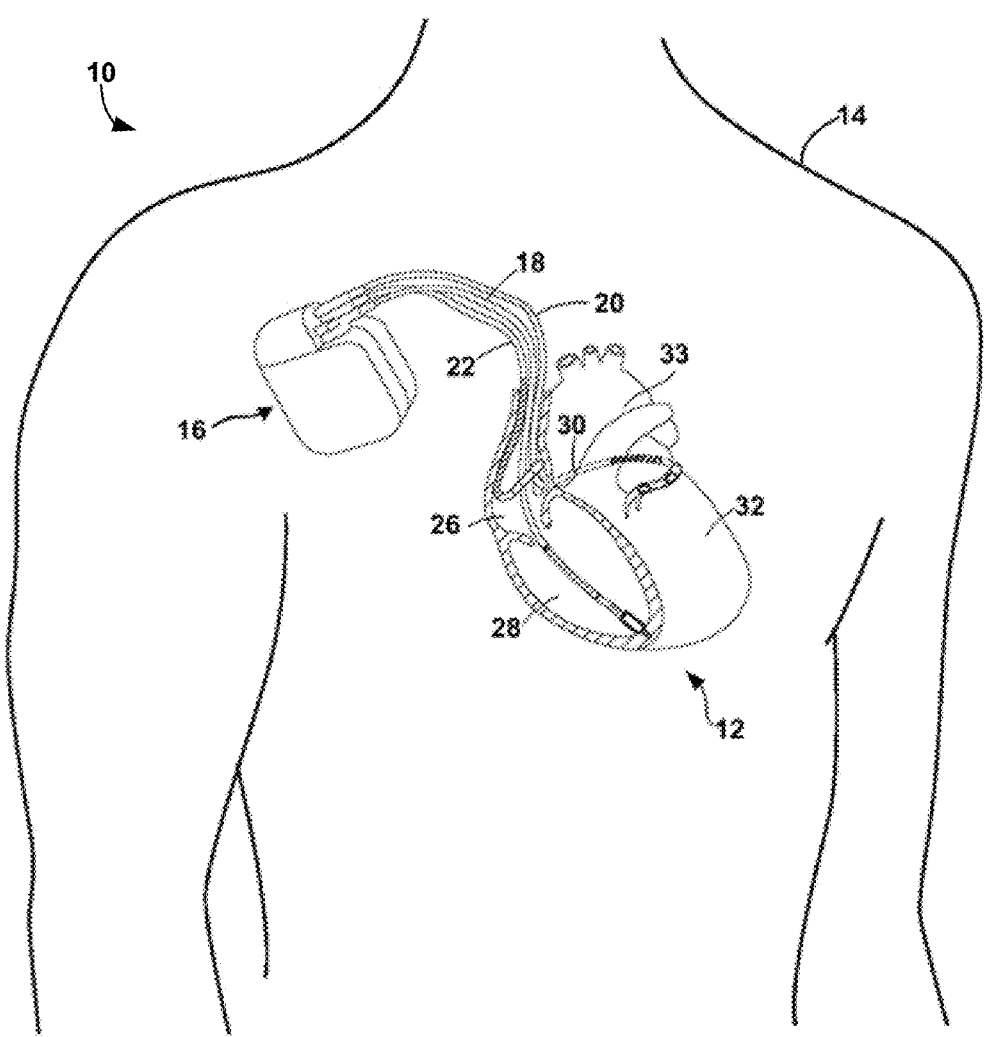
FIG. 9 is a diagram of an exemplary system including an exemplary implantable medical device (IMD).

FIG. 9 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that provides electrical signals to the heart 12 of the patient 14 via electrodes coupled to one or more of the leads 18, 20, 22 (e.g., electrodes that may be implanted in accordance with the description herein, such as, with use of noninvasive selection of implantation site regions).

The leads 18, 20, 22 extend into the heart 12 of the patient 14 to sense electrical activity of the heart 12 and/or to deliver electrical stimulation to the heart 12. In the example shown in FIG. 15, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripoloar, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 10A:
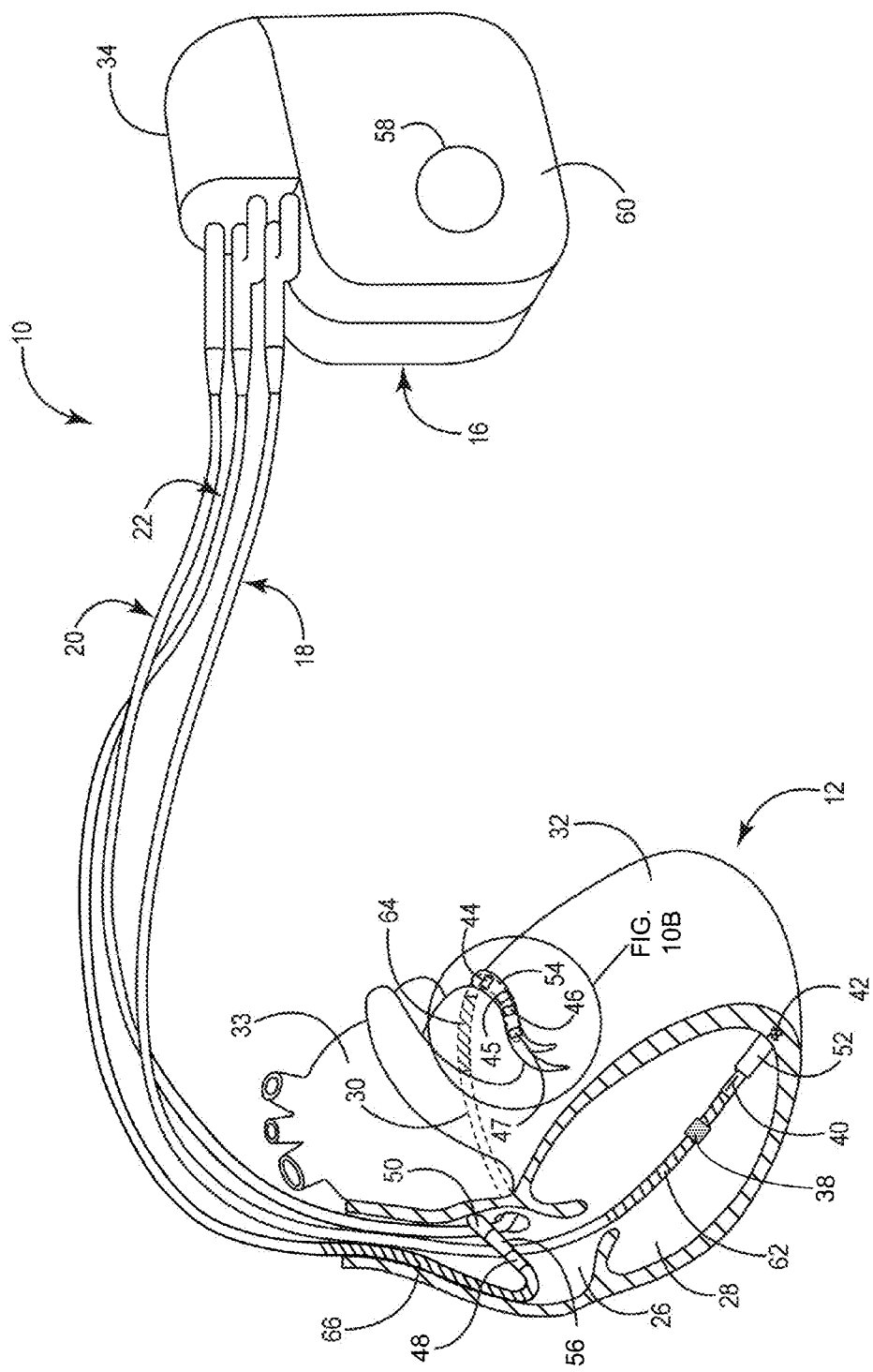
FIG. 10A is a diagram of the exemplary IMD of FIG. 9.
Figure 10B:
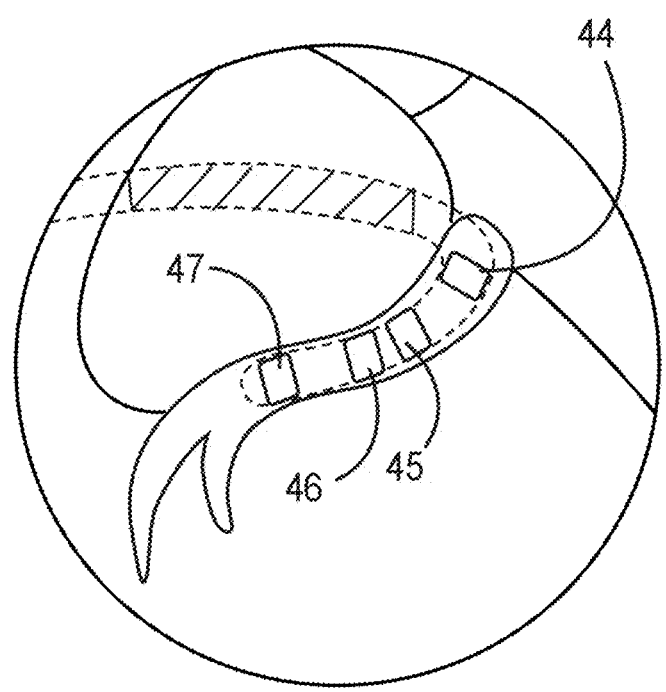
FIG. 10B is a diagram of an enlarged view of a distal end of the electrical lead disposed in the left ventricle of FIG. 10A.

FIGS. 10A-10B are conceptual diagrams illustrating the IMD 16 and the leads 18, 20, 22 of therapy system 10 of FIG. 15 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 $mm^2$ to about 5.8 $mm^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50, 58 may further be used to sense electrical signals (e.g., morphological waveforms within electrograms (EGM)) attendant to the depolarization and repolarization of the heart 12. The sensed electrical signals may be used to determine which of the electrodes 40, 42, 44, 45, 46, 47, 48, 50 are the most effective in improving cardiac function. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 10A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIG. 10A, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

The configuration of the exemplary therapy system 10 illustrated in FIGS. 9-11 is merely one example. In other examples, the therapy system may include epicardial leads and/or patch electrodes instead of or in addition to the transvenous leads 18, 20, 22 illustrated in FIG. 9. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 9). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

Figure 11A:
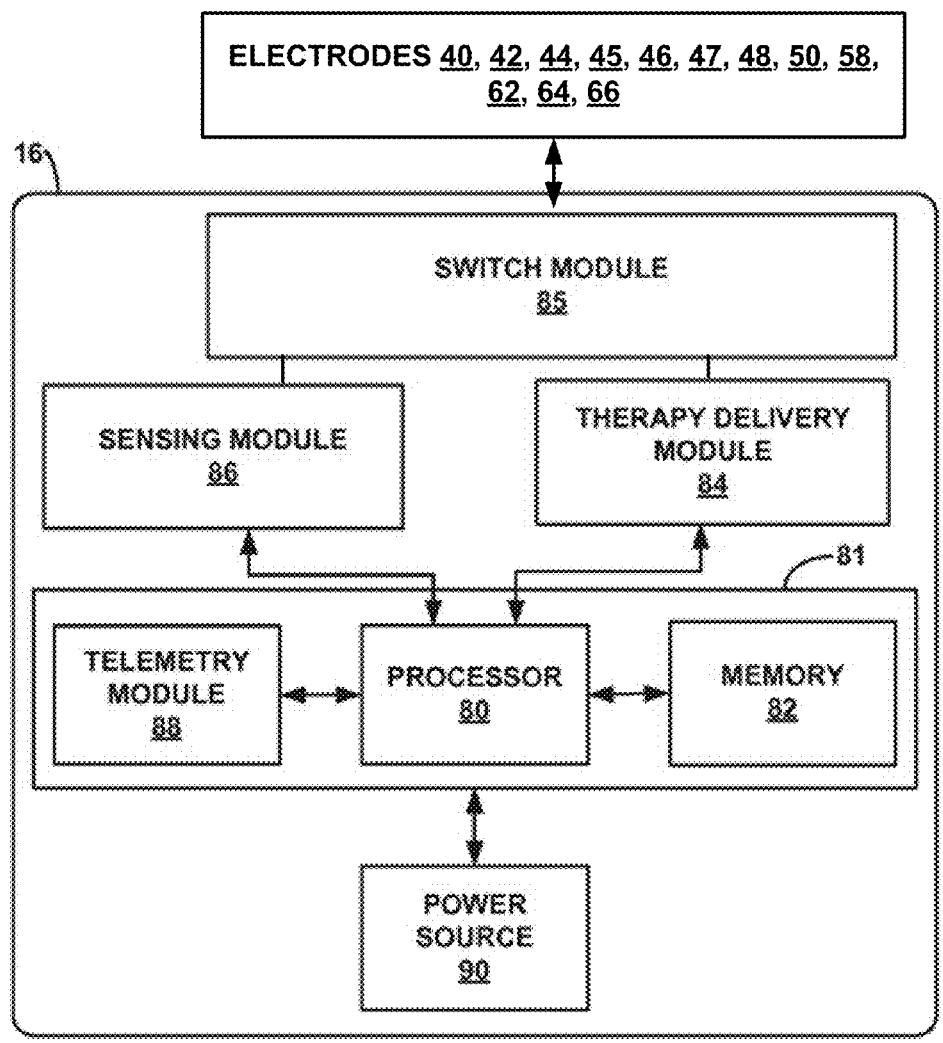
FIG. 11A is a block diagram of an exemplary IMD, e.g., the IMD of FIGS. 9-10.

FIG. 11A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 42 and 50 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 11B:
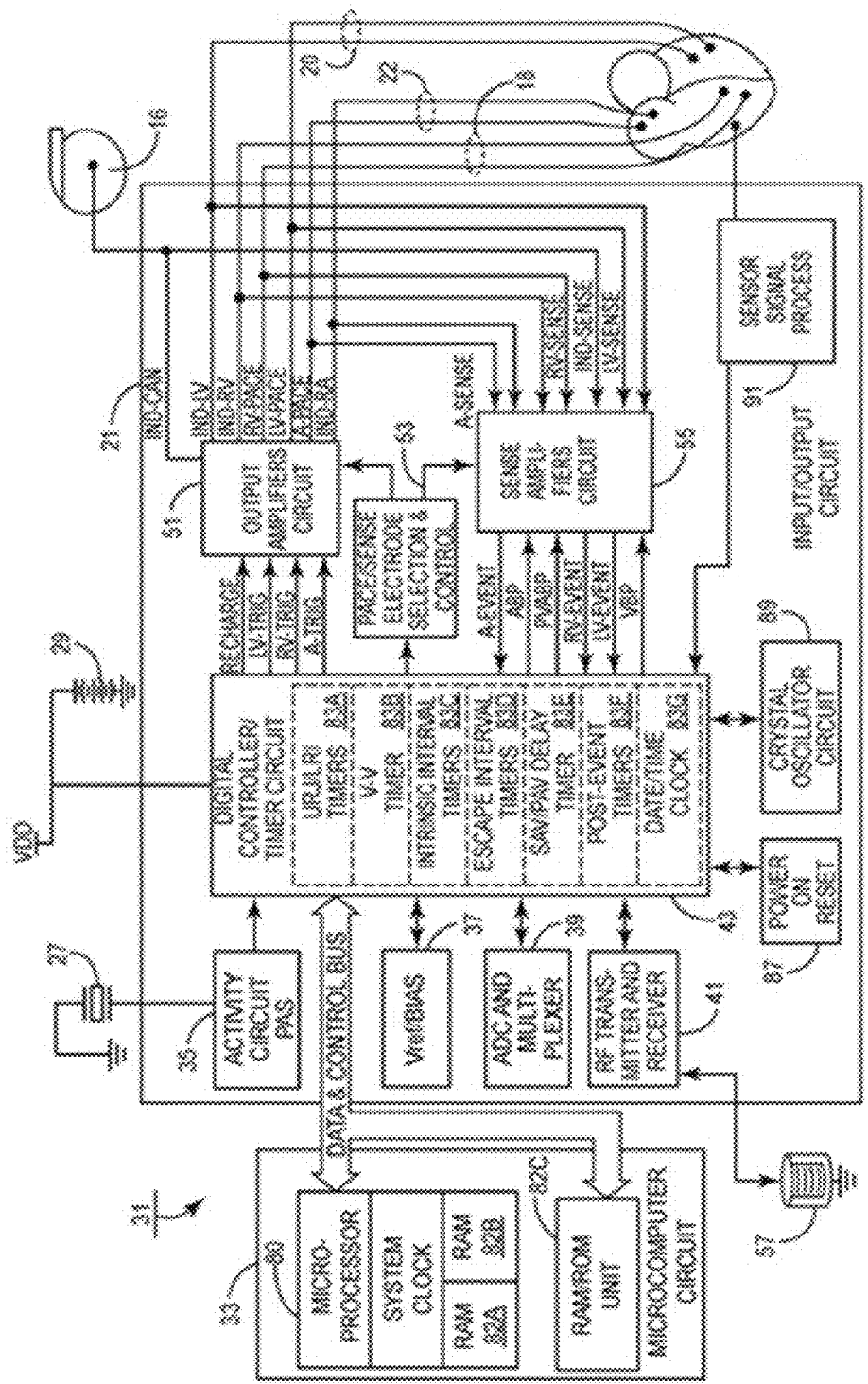
FIG. 11B is another block diagram of an exemplary IMD (e.g., an implantable pulse generator) circuitry and associated leads employed in the system of FIGS. 9-10 for providing three sensing channels and corresponding pacing channels.

FIG. 11B is another embodiment of a functional block diagram for IMD 16. FIG. 11B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which are incorporated herein by reference in their entireties. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed:

1. A system for assisting in noninvasive evaluation of cardiac therapy comprising:
    electrode apparatus comprising a plurality of external surface electrodes positioned in an array, wherein the electrode apparatus is configured to locate the plurality of external surface electrodes proximate the skin of the patient;
    a display apparatus comprising a graphical user interface configured to present cardiac electrical activation time information and cardiac health information; and
    computing apparatus coupled to the electrode apparatus and the display apparatus and configured to provide the graphical user interface displayed on the display apparatus to assist a user in noninvasively evaluating cardiac therapy, wherein the computing apparatus is further configured to:
        noninvasively measure surrogate cardiac electrical activation times using one or more external surface electrodes of the plurality of external surface electrodes of the electrode apparatus proximate the patient's heart, wherein the surrogate cardiac electrical activation times are representative of depolarization of cardiac tissue that propagates through the torso of the patient, noninvasively measure at least one metric of the patient's cardiac health using one or more external surface electrodes of the plurality of external surface electrodes of the electrode apparatus proximate the patient's heart, determine whether cardiac therapy for the patient is beneficial based on a comparison of presently-measured noninvasive measurements made using the one or more external surface electrodes of the plurality of external surface electrodes and previously-measured noninvasive measurements made using the one or more external surface electrodes of the plurality of external surface electrodes of the electrode apparatus, and simultaneously display, on the graphical user interface,
an indication of whether cardiac therapy for the patient is beneficial based on the comparison of presently-measured noninvasive measurements and previously-measured noninvasive measurements,
a graphical depiction of a portion of a first human anatomy and presently-measured surrogate cardiac electrical activation times about the first human anatomy portion that were noninvasively measured using the one or more external surface electrodes of the plurality of external surface electrodes proximate the skin of the patient,
a graphical depiction of a portion of a second human anatomy and previously-measured surrogate cardiac electrical activation times about the second human anatomy portion that were noninvasively measured using the one or more external surface electrodes of the plurality of external surface electrodes proximate the skin of the patient,
the at least one presently-measured metric of the patient's cardiac health that was noninvasively measured using the one or more external surface electrodes of the plurality of external surface electrodes proximate the skin of the patient, and
the at least one previously-measured metric of the patient's cardiac health that was noninvasively measured using the one or more external surface electrodes of the plurality of external surface electrodes proximate the skin of the patient.

2. The system of claim 1, wherein the indication of whether cardiac therapy for the patient is beneficial comprises a percentage improvement between the at least one previously-measured metric of the patient's cardiac health and the at least one presently-measured metric of the patient's cardiac health.

3. The system of claim 1, wherein the computing apparatus is further configured to allow the user to change at least one pacing parameter of an implantable medical device providing cardiac therapy to the patient.

4. The system of claim 3, wherein the at least one pacing parameter comprises at least one of a pacing timing interval, a pacing vector, and a pacing mode.

5. The system of claim 1, wherein the computing apparatus is further configured to display, on the graphical user interface, mechanical motion information of one or more regions of at least a portion of blood vessel anatomy of the patient's heart.

6. The system of claim 1, wherein the first human anatomy portion and the second human anatomy portion depict the same human anatomy.

7. The system of claim 1, wherein displaying graphical depictions of the measured surrogate cardiac electrical activation times about the first and second human anatomy portions comprises displaying graphical depictions of the measured surrogate cardiac electrical activation times about graphical depictions of at least one of an anterior side of a human torso and a posterior side of a human torso.

8. The system of claim 1, wherein displaying graphical depictions of the measured surrogate cardiac electrical activation times about the first and second human anatomy portions comprises displaying graphical depictions of the measured surrogate cardiac electrical activation times about graphical depictions of at least one of an anterior side of a heart and a posterior side of a heart.

9. The system of claim 1, wherein the at least one metric comprises QRS width and electrical dyssynchrony.

10. The system of claim 1, wherein displaying the graphical depictions of the measured surrogate cardiac electrical activation times about a portion of human anatomy comprises color scaling the portions of human anatomy on the graphical user interface according to the measured surrogate cardiac electrical activation times.

11. The system of claim 1, wherein the computing apparatus is further configured to display, on the graphical user interface, at least one electrocardiogram of the patient, wherein each of the at least one electrocardiogram are captured using at least one different electrode, and wherein the at least one electrocardiogram is time-aligned on the graphical user interface.

12. A method for assisting in noninvasive evaluation of cardiac therapy comprising:
noninvasively measuring surrogate cardiac electrical activation times using one or more external surface electrodes proximate the skin of the patient and proximate the patient's heart, wherein the surrogate cardiac electrical activation times are representative of depolarization of cardiac tissue that propagates through the torso of the patient;
noninvasively measuring at least one metric of the patient's cardiac health using one or more external surface electrodes proximate the skin of the patient and proximate the patient's heart;
determining whether cardiac therapy for the patient is beneficial based on a comparison of presently-measured noninvasive measurements made using the one or more external surface electrodes proximate the skin of the patient and previously-measured noninvasive measurements made using the one or more external surface electrodes proximate the skin of the patient; and
simultaneously displaying, on a graphical user interface,
an indication of whether cardiac therapy for the patient is beneficial based on the comparison,
a graphical depiction of a portion of a first human anatomy and the presently-measured surrogate cardiac electrical activation times about the first human anatomy portion that were noninvasively measured using the one or more external surface electrodes proximate the skin of the patient,
a graphical depiction of a portion of a second human anatomy and the previously-measured surrogate cardiac electrical activation times about the second human anatomy portion that were noninvasively measured using the one or more external surface electrodes proximate the skin of the patient, the at least one presently-measured metric of the patient's cardiac health that was noninvasively measured using the one or more external surface electrodes proximate the skin of the patient, and the at least one previously-measured metric of the patient's cardiac health that was noninvasively measured using the one or more external surface electrodes proximate the skin of the patient.

13. The method of claim 12, wherein the indication of whether cardiac therapy for the patient is beneficial comprises a percentage improvement between the at least one previously-measured metric of the patient's cardiac health and the at least one presently-measured metric of the patient's cardiac health.

14. The method of claim 12, wherein the method further comprises allowing the user to change at least one pacing parameter of an implantable medical device providing cardiac therapy to the patient.

15. The method of claim 12, wherein the method further comprises displaying, on the graphical user interface, mechanical motion information of one or more regions of at least a portion of blood vessel anatomy of the patient's heart.

16. The method of claim 12, wherein displaying graphical depictions of the measured surrogate cardiac electrical activation times about the first and second human anatomy portions comprises displaying graphical depictions of the measured surrogate cardiac electrical activation times about graphical depictions of at least one of an anterior side of a human torso, a posterior side of a human torso, an anterior side of a heart, and a posterior side of a heart.

17. The method of claim 12, wherein the at least one metric comprises QRS width and electrical dyssynchrony.

18. The method of claim 12, wherein displaying the graphical depictions of the measured surrogate cardiac electrical activation times about a portion of human anatomy comprises color scaling the portions of human anatomy on the graphical user interface according to the measured surrogate cardiac electrical activation times.

19. The method of claim 12, wherein the method further comprises displaying, on the graphical user interface, at least one electrocardiogram of the patient, wherein each of the at least one electrocardiogram are captured using at least one different electrode, and wherein the at least one electrocardiogram is time-aligned on the graphical user interface.

20. A system for assisting in noninvasive evaluation of a patient for cardiac therapy comprising:

means for noninvasively measuring surrogate cardiac electrical activation times representative of electrical activation times of a patient's heart from the patient's skin;

means for noninvasively measuring at least one metric of the patient's cardiac health from the patient's skin, wherein the surrogate cardiac electrical activation times are representative of depolarization of cardiac tissue that propagates through the torso of the patient;

means for determining whether cardiac therapy for the patient is beneficial based on a comparison of presently-measured noninvasive measurements made and previously-measured noninvasive measurements that were noninvasively measured from the patient's skin; and display means for simultaneously displaying, on a graphical user interface, a graphical depiction of a portion of a first human anatomy and presently-measured surrogate cardiac electrical activation times about the first human anatomy portion that were noninvasively measured from the patient's skin, a graphical depiction of a portion of a second human anatomy and previously-measured surrogate cardiac electrical activation times about the second human anatomy portion that were noninvasively measured from the patient's skin, the at least one presently-measured metric of the patient's cardiac health that was noninvasively measured from the patient's skin, the at least one previously-measured metric of the patient's cardiac health that was noninvasively measured from the patient's skin, and an indication of whether cardiac therapy for the patient is beneficial based on the comparison.

21. The system of claim 1, wherein the indication of whether cardiac therapy for the patient is beneficial comprises one or more of an indication that a location of an implantable lead delivering cardiac therapy is providing beneficial cardiac therapy to the patient, an indication that one or more settings of the cardiac therapy being delivered to the patient are beneficial, and an indication that one or more adjustments to the cardiac therapy are beneficial to the patient.

* * * * *